(12) United States Patent
Ramsey et al.

(10) Patent No.: US 11,053,535 B2
(45) Date of Patent: Jul. 6, 2021

(54) DEVICES WITH A FLUID TRANSPORT NANOCHANNEL INTERSECTED BY A FLUID SENSING NANOCHANNEL AND RELATED METHODS

(75) Inventors: John Michael Ramsey, Chapel Hill, NC (US); Jean Pierre Alarie, Chapel Hill, NC (US); Laurent Menard, Cary, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 588 days.

(21) Appl. No.: 14/342,032

(22) PCT Filed: Sep. 7, 2012

(86) PCT No.: PCT/US2012/054128
§ 371 (c)(1),
(2), (4) Date: Apr. 9, 2014

(87) PCT Pub. No.: WO2013/039778
PCT Pub. Date: Mar. 21, 2013

(65) Prior Publication Data
US 2014/0234980 A1 Aug. 21, 2014

Related U.S. Application Data

(60) Provisional application No. 61/533,523, filed on Sep. 12, 2011.

(51) Int. Cl.
*C12Q 1/68* (2018.01)
*G01N 27/447* (2006.01)
(Continued)

(52) U.S. Cl.
CPC .......... *C12Q 1/68* (2013.01); *G01N 27/44791* (2013.01); *G01N 33/48721* (2013.01); *Y10T 436/143333* (2015.01)

(58) Field of Classification Search
CPC ....... G01N 27/44791; G01N 33/48721; C12Q 1/68; Y10T 436/143333
(Continued)

(56) References Cited

U.S. PATENT DOCUMENTS 5,296,116 A 3/1994 Guttman
5,858,187 A * 1/1999 Ramsey .............. B01F 13/0062
204/451

(Continued)

FOREIGN PATENT DOCUMENTS

JP 2003-166934 A 6/2003
JP 2005-102619 4/2005
(Continued)

OTHER PUBLICATIONS

Abgrall et al. "Nanofluidic Devices and Their Applications", *Anal. Chem.*, 2008, 80:2326-2341.
(Continued)

*Primary Examiner* — Rebecca M Fritchman
(74) *Attorney, Agent, or Firm* — Myers Bigel, P.A.

(57) ABSTRACT

Devices, such as chips for DNA analysis, have at least one fluid transport nanochannel with at least one intersecting (e.g., transverse) sensing nanochannel that can be monitored for change in ionic current to determine characteristics or
(Continued)

parameters of interest, e.g., molecular identification, length determination, localized (probe) mapping and the like.

17 Claims, 13 Drawing Sheets

(51) Int. Cl.
  *G01N 33/487* (2006.01)
  *C12Q 1/00* (2006.01)
(58) Field of Classification Search
  USPC .............................................. 436/94; 216/66
  See application file for complete search history.

(56) References Cited

U.S. PATENT DOCUMENTS

| | | | |
|---|---|---|---|
| 5,872,010 A | 2/1999 | Karger et al. | |
| 5,900,130 A | 5/1999 | Benvegnu et al. | |
| 6,074,827 A | 6/2000 | Nelson et al. | |
| 6,500,323 B1 | 12/2002 | Chow et al. | |
| 6,524,456 B1 | 2/2003 | Ramsey et al. | |
| 6,537,433 B1 | 3/2003 | Bryning et al. | |
| 6,592,733 B1 | 7/2003 | Foley et al. | |
| 6,790,671 B1 | 9/2004 | Austin et al. | |
| 6,803,568 B2 | 10/2004 | Luc et al. | |
| 6,846,398 B1 | 1/2005 | Heller et al. | |
| 6,994,826 B1 | 2/2006 | Hasselbrink et al. | |
| 7,033,474 B1 | 4/2006 | Dubrow et al. | |
| 7,160,423 B2 | 1/2007 | Chien et al. | |
| 7,229,540 B2 | 6/2007 | Okamoto et al. | |
| 7,465,381 B2 | 12/2008 | Lopez et al. | |
| 7,670,770 B2* | 3/2010 | Chou ................ C12Q 1/6869 422/68.1 | |
| 7,744,762 B2 | 6/2010 | Lazar | |
| 7,960,105 B2 | 6/2011 | Schwartz et al. | |
| 8,246,799 B2 | 8/2012 | Oliver et al. | |
| 8,333,934 B2 | 12/2012 | Cao et al. | |
| 8,691,588 B2 | 4/2014 | Park et al. | |
| 8,722,327 B2 | 5/2014 | Cao et al. | |
| 8,735,065 B2 | 5/2014 | Craighead et al. | |
| 8,764,968 B2 | 7/2014 | Afzali-Ardakani et al. | |
| 8,940,147 B1* | 1/2015 | Bartsch .............. G01N 27/44791 204/601 | |
| 9,061,901 B2 | 6/2015 | Cao et al. | |
| 9,970,898 B2 | 5/2018 | Ramsey et al. | |
| 10,571,428 B2 | 2/2020 | Ramsey et al. | |
| 2002/0000516 A1 | 1/2002 | Schultz et al. | |
| 2002/0061529 A1 | 5/2002 | Bridgham et al. | |
| 2002/0072243 A1 | 6/2002 | Craighead et al. | |
| 2002/0081744 A1 | 6/2002 | Chan et al. | |
| 2002/0160365 A1 | 10/2002 | O'Brien | |
| 2002/0190204 A1 | 12/2002 | Hofstadler et al. | |
| 2002/0197603 A1 | 12/2002 | Chow et al. | |
| 2003/0075446 A1* | 4/2003 | Culbertson ........ B01L 3/502761 204/451 | |
| 2003/0136679 A1* | 7/2003 | Bohn ................... B01D 57/02 204/543 | |
| 2003/0146377 A1 | 8/2003 | Miller et al. | |
| 2004/0033515 A1 | 2/2004 | Cao et al. | |
| 2004/0166504 A1 | 8/2004 | Rossier et al. | |
| 2005/0023156 A1 | 2/2005 | Ramsey et al. | |
| 2005/0082204 A1 | 4/2005 | Schwartz et al. | |
| 2005/0103713 A1 | 5/2005 | Ramsey et al. | |
| 2005/0196746 A1 | 9/2005 | Xu et al. | |
| 2006/0084078 A1 | 4/2006 | Zhao | |
| 2006/0169587 A1 | 8/2006 | Lopez et al. | |
| 2006/0240573 A1 | 10/2006 | Kao et al. | |
| 2006/0275778 A1 | 12/2006 | Wu et al. | |
| 2006/0278879 A1 | 12/2006 | Busta | |
| 2007/0057179 A1 | 3/2007 | Bousse et al. | |
| 2007/0145263 A1 | 6/2007 | Weng | |
| 2007/0192911 A1 | 8/2007 | Jin et al. | |
| 2008/0057192 A1 | 3/2008 | Faguet | |
| 2009/0023146 A1 | 1/2009 | Harnack et al. | |
| 2009/0111115 A1 | 4/2009 | Drmanac et al. | |
| 2009/0115094 A1 | 5/2009 | Chou et al. | |
| 2009/0136682 A1* | 5/2009 | Branton ........... G01N 33/48721 427/532 | |
| 2009/0305273 A1* | 12/2009 | Cao .................... B01L 3/502761 435/6.14 | |
| 2010/0029508 A1 | 2/2010 | Austin et al. | |
| 2010/0029915 A1 | 2/2010 | Duthie et al. | |
| 2010/0075428 A1 | 3/2010 | Wang et al. | |
| 2010/0159462 A1 | 6/2010 | Takayama et al. | |
| 2010/0267158 A1 | 10/2010 | Chou et al. | |
| 2011/0036994 A1 | 2/2011 | Frayling | |
| 2011/0155575 A1* | 6/2011 | Dorairaj ............... G01N 27/447 204/453 | |
| 2011/0201509 A1 | 8/2011 | Tegenfeldt et al. | |
| 2011/0226623 A1 | 9/2011 | Timp et al. | |
| 2011/0227558 A1 | 9/2011 | Mannion et al. | |
| 2011/0296903 A1 | 12/2011 | Cao et al. | |
| 2011/0308949 A1 | 12/2011 | Afzali-Ardakani et al. | |
| 2012/0193231 A1 | 8/2012 | Afzali-Ardakani et al. | |
| 2012/0196376 A1 | 8/2012 | Park et al. | |
| 2013/0068618 A1 | 3/2013 | Harrer et al. | |
| 2013/0195723 A1 | 8/2013 | Ramsey et al. | |
| 2013/0224736 A1 | 8/2013 | Marie et al. | |
| 2014/0194313 A1 | 7/2014 | Craighead et al. | |
| 2014/0194314 A1 | 7/2014 | Walsworth et al. | |
| 2014/0197105 A1 | 7/2014 | DiBiasio et al. | |
| 2014/0238856 A1 | 8/2014 | Ramsey et al. | |
| 2014/0272958 A1 | 9/2014 | Ramsey et al. | |
| 2015/0008124 A1 | 1/2015 | Oliver | |
| 2016/0024569 A1 | 1/2016 | Ramsey et al. | |

FOREIGN PATENT DOCUMENTS

| | | |
|---|---|---|
| JP | 2005241255 A | 9/2005 |
| JP | 2007-149861 | 6/2007 |
| WO | WO 96/04547 A1 | 2/1996 |
| WO | WO 00/02038 A1 | 1/2000 |
| WO | WO 01/13088 A1 | 2/2001 |
| WO | WO 03/025540 A2 | 3/2003 |
| WO | WO 2007/011622 A2 | 1/2007 |
| WO | WO 2008/079169 A2 | 7/2008 |
| WO | WO 2008/132734 A2 | 11/2008 |
| WO | WO 2009/030953 A1 | 3/2009 |
| WO | WO 2009/120642 | 10/2009 |
| WO | WO 2012/040098 A2 | 3/2012 |
| WO | WO 2012/055415 A1 | 5/2012 |
| WO | WO 2013/039778 | 3/2013 |
| WO | WO 2013/088098 A2 | 6/2013 |
| WO | WO 2013/119765 A1 | 8/2013 |
| WO | WO 2013/176767 A1 | 11/2013 |
| WO | WO 2013/191908 A1 | 12/2013 |

OTHER PUBLICATIONS

Balducci et al. "Double-Stranded DNA Diffusion in Slitlike Nanochannels", *Macromolecules*, 2006, 39:6273-6281.
Cross et al. "Size-dependent DNA mobility in nanochannels", *Journal of Applied Physics*, 102:024701-1-024701-5; (2007).
Cui "Counterion-Hopping along the Backbone of Single-Stranded DNA in Nanometer Pores: A Mechanism for Current Conduction", *Physical Review Letters*, 98:138101, 2007.
Douville et al. "DNA linearization through confinement in nanofluidic channels", *Anal Bioanal Chem.*, 2008, 391:2395-2409.
Fan et al. "DNA Translocation in Inorganic Nanotubes", *Nano Letters*, vol. 5, No. 9, Sep. 2005, 5 pages.
Gierak et al. "Sub-5 nm FIB direct patterning of nanodevices", *Microelectronic Engineering*, vol. 84, Issue 5-8, May-Aug. 2007, 779-783.
Han et al. "Prediction of nanopattern topography using two-dimensional focused ion beam milling with beam irradiation intervals", *Microelectronic Engineering*, vol. 87, Issue 1, Jan. 2010, 1-9.
Haneveld et al. "Wet anisotropic etching for fluidic 1D nanochannels", *J. Micromech. Microeng.*, 13, 2003, S62-S66.
Holzer et al. "Three-dimensional analysis of porous BaTiO$_3$ ceramics using FIB nanotomography", *Journal of Microscopy*, vol. 216, Pt. 1, Oct. 2004, 84-95.

(56) References Cited

OTHER PUBLICATIONS

Huh et al. "Tuneable elastomeric nanochannels for nanofluidic manipulation", *Nature Materials*, vol. 6, Jun. 2007, 424-428.
Lagerqvist et al. "Fast DNA Sequencing via Transverse Electronic Transport", *Nano Letters*, vol. 6, No. 4, 2006, 779-782.
Lerman et al. "Why Does the Electrophoretic Mobility of DNA in Gels Vary with the Length of the Molecule?", *Biopolymers*, vol. 21, 995-997, 1982.
Li et al. "Focused ion beam fabrication of silicon print masters", *Nanotechnology*, 14, 2003, 220-223.
Lugstein et al. "FIB processing of silicon in the nanoscale regime", *Applied Physics A*, 76:545-548, 2003.
Menard et al. "Analysis of Single DNA Molecules Translocating Through Nanochannels Fabricated in $SiO_2$", *Twelfth International Conference on Miniaturized Systems for Chemistry and Life Sciences*, Oct. 12-16, 2008, San Diego, California, 4 pages.
Menard Jr. et al. "DNA Transport Characteristics in Focused Beam-Milled Nanofluidic Devices", *2009 Annual Meeting of the American Electrophoresis Society (AES)*, Nov. 10, 2009, Retrieved from the internet at URL http://aiche.confex.com/aiche/2009/webprogram/Paaper160572.html.
Mijatovic et al. "Technologies for nanofluidic systems: *top-down* vs. *bottom-up* —a review", *Lab Chip*, 2005, 5, 492-500.
Nakayama et al. "Stability and Schottky barrier of silicides: First-principles study", *Microelectronic Engineering*, vol. 86, Issues 7-9, Jul.-Sep. 2009, pp. 1718-1721.
Orloff et al. "Fundamental limits to imaging resolution for focused ion beams", *Journal of Vacuum Science & Technology B*, 14, 3759-3763 (1996).
Perry et al. "Review of fabrication of nanochannels for single phase liquid flow", *Microfluid Nanofluid*, 2006, 2:185-193.
Randolph et al. "Focused, Nanoscale Electron-Beam-Induced Deposition and Etching", *Critical Reviews in Solid State and Materials Sciences*, 31:3, 55-89, 2006.
Reisner et al. "Nanoconfinement-Enhanced Conformational Response of Single DNA Molecules to Changes in Ionic Environment", *Physical Review Letters*, 99, 058302, 2007.
Salieb-Beugelaar et al. "Field-Dependent DNA Mobility in 20 nm High Nanoslits", *Nano Letters*, vol. 8, No. 7, Jul. 2008.
Strychalski et al. "Diffusion of DNA in Nanoslits", *Macromolecules*, 2008, 41:7716-7721.
Tseng "Recent developments in micromilling using focused ion beam technology", *Journal of Micromechanics and Microengineering*, 14:R15-R34, 2004.
Wang et al. "Manipulating DNA molecules in nanofluidic channels", *Microfluid Nanofluid*, 2:85-88; 2006.
Xu et al. "Wide-spectrum, ultrasensitive fluidic sensors with amplification from both fluidic circuits and metal oxide semiconductor field effect transistors", *Applied Physics Letters*, 91:013901, 2007.
Campbell et al. "Electrophoretic manipulation of single DNA molecules in nanofabricated capillaries", *Lab Chip*, 2004, 4:225-229.
Cao et al. "Fabrication of 10 nm enclosed nanofluidic channels", *Applied Physics Letters*, vol. 81, No. 1, Jul. 2002, pp. 174-176.
Craighead et al. "Future lab-on-a-chip technologies for interrogating individual molecules" Nature 2006, 442, 387.
Duke et al. "Microchips for Sorting DNA" pp. 11-26, 1997.
Eijkel et al. "Nanofluidics: what is it and what can we expect from it?" Microfluid. Nanofluid. 2005, 1, 249.
Fischbein et al. "Sub-10 nm Device Fabrication in a Transmission Electron Microscope" Nano Letters 2007, vol. 7, 1329.
Gierhart et al. "Nanopore with transverse nanoelectrodes for electrical characterization and sequencing of DNA" Sens. and Actuators B 2008, 132, 593.
Kasianowicz et al., "Nanoscopic Porous Sensors", *Annu. Rev. Anal. Chem.*, 2008, vol. 1, pp. 737-766.
Kovarik et al. "Nanofluidics in Lab-on-a-Chip Devices" Analytical chemistry feature, 2009, 81, 7133-7140.

Lerman et al., Communications to the Editor "Why Does the Electrophoretic Mobility of DNA in Gels Vary with the Length of the Molecule?" Biopolymers 1982, 21, 995-997.
Levy et al. "Entropic Unfolding of DNA Molecules in Nanofluidic Channels" Nano Letters, 2008, 8, 3839.
Li et al. "Sacrificial polymers for nanofluidic channels in biological applications" Nanotechnology 2003, 14, 578.
Liang et al. "Single Sub-20 nm Wide, Centimeter-Long Nanofluidic Channel Fabricated by Novel Nanoimprint Mold Fabrication and Direct Imprinting", Nano Letters, 2007, vol. 7, 3774.
Liang et al., "Nanogap detector inside nanofluidic channel for fast real-time label-free DNA analysis", *Nano Letters*, 2008, vol. 8, No. 5, pp. 1472-1476.
Maleki et al., "A nanofluidic channel with embedded transverse nanoelectrodes", *Nanotechnology*, 2009, vol. 20:105302, pp. 1-6.
Mannion et al. "Conformational Analysis of Single DNA Molecules Undergoing Entropically Induced Motion in Nanochannels" Biophysical Journal, 2006, 90, 4538.
Mao et al. "Fabrication and characterization of 20 nm planar nanofluidic channels by glass-glass and glass-silicon bonding" Lab Chip 2005, 5, 837.
Nikoobakht, B., "A Scalable Platform for Integrating Horizontal Nanochannels with Known Registries to Microchannels", *Chem. Mater.*, 2009, vol. 21, pp. 27-32.
Persson et al. "Confinement Spectroscopy: Probing Single DNA Molecules with Tapered Nanochannels", Nano Letters, 2009, vol. 9, No. 4, 1382-1385.
Reisner et al. "Statics and Dynamics of Single DNA Molecules Confined in Nanochannels" Physical Review Letters, 2005, 94, 196101.
Riehn et al., "Restriction mapping in nanofluidic devices", *PNAS*, Jul. 19, 2005; vol. 102, No. 29, pp. 10012-10016.
Salieb-Beugelaar et al. "Electrophoretic separation of DNA in gels and nanostructures", Lab Chip 2009, 9, 2508-2523.
Schoch et al. "Transport phenomena in nanofluidics" Reviews of Modern Physics, 2008, 80, 839-883.
Smeets et al. "Salt Dependence of Ion Transport and DNA Translocation through Solid State Nanopores" Nano Letters 2006, vol. 6, No. 1, 89.
So et al. "Inherently aligned microfluidic electrodes composed of liquid metal", Lab Chip, 2011, 11, 905-911.
Striemer et al. "Charge- and size-based separation of macromolecules using ultrathin silicon membranes" Nature, 2007, 445, 749-753.
Tong et al. "Silicon Nitride Nanosieve Membrane" Nano Letters 2004 vol. 4, No. 2 pp. 283-287.
Tsutsui et al. "Transverse Field Effects on DNA-Sized Particle Dynamics" Nano Letters 2009, vol. 9, No. 4, 1659.
Volkmuth et al. "DNA electrophoresis in microlithographic arrays" Nature 1992, 358, 600-602.
Wang et al., "Single-molecule studies of repressor-DNA interactions show long-range interactions", *PNAS*, Jul. 12, 2005; vol. 102, No. 28, pp. 9796-9801.
Yuan et al. "Electrokinetic transport and separations in fluidic nanochannels" Electrophoresis 2007, 28, 595-610.
Zwolak, M., "Electronic Signature of DNA Nucleotides via Transverse Transport", *Nano Letters*, 2005, vol. 5, No. 3, pp. 421-424.
International Search Report for corresponding PCT Application No. PCT/US2012/054128, dated Feb. 21, 2013.
Menard et al., Fabrication of Sub-5 nm Nanochannels in Insulating Substrates Using Focused Ion Beam Milling, Nano Lett, 2011, vol. 11, pp. 512-517.
Taniguchi et al., Fabrication of the gating nanopore device, Applied Physics Letters, 2009, vol. 95, pp. 123701-1-123701-3.
Alkan et al., "Genome structural variation discovery and genotyping", *Nat. Rev. Genet.*, 2011, vol. 12, pp. 363-376.
Apel et al., "Diode-like single-ion track membrane prepared by electro☐stopping", *Nucl. Instrum. Methods Phys. Res.*, Sect. B, 2001, 184, 337-346.
Baday et al., "Multicolor super-resolution DNA imaging for genetic analysis", *Nano Lett.*, 2012, vol. 12, pp. 3861-3866.

(56) References Cited

OTHER PUBLICATIONS

Balducci et al., "Conformational preconditioning by electrophoresis of DNA through a finite obstacle array", *Macromolecules*, 2008, vol. 41, pp. 5485-5492.

Brochard et al., "Dynamics of confined polymer chains", *J. Chem. Phys.*, Jul. 1977, vol. 67, pp. 52-56.

Brochard-Wyart et al., "Dynamics of Taut DNA chains", *Europhys. Lett.*, 1999, vol. 47(2), pp. 171-174.

Cao et al., "Gradient nanostructures for interfacing microfluidics and nanofluidics", *Appl. Phys. Lett.*, Oct. 14, 2002; vol. 81, No. 16, pp. 3058-3060.

Chantiwas et al., "Flexible fabrication and applications of polymer nanochannels and nanoslits", *Chem. Soc. Rev.*, 2011, vol. 40, pp. 3677-3702.

Chou et al., "A microfabricated device for sizing and sorting DNA molecules", *Proc. Natl. Acad. Sci.*, 1999, vol. 96, pp. 11-13.

Cipriany et al., "Single molecule epigenetic analysis in a nanofluidic channel", Anal. Chem., Mar. 15, 2010, vol. 82, No. 6, pp. 2480-2487.

Craddock et al., "Genome-wide association study of CNVs in 16,000 cases of eight common diseases and 3,000 shared controls", *Nature*, 2010, vol. 464, pp. 713-720.

Das et al., "Single molecule linear analysis of DNA in nano-channel labeled with sequence specific fluorescent probes", *Nucl. Acids Res.*, 2010, vol. 38, e177, 8 pages.

Dimalanta et al., "A microfluidic system for large DNA molecule arrays", *Anal. Chem.*, 2004, vol. 76, pp. 5293-5301.

Foquet et al., "DNA fragment sizing by single molecule detection in submicrometer-sized closed fluidic channels", *Anal. Chem.*, 2002, vol. 74, pp. 1415-1422.

Freitag et al., "Meandering nanochannels for imaging of ultra-long DNA molecules", *Proceedings of the 15th International Conference on Miniaturized Systems for Chemistry and Life Sciences*, Oct. 2-6, 2011, Seattle, Washington; Landers, J. P., Herr, A., Juncker, D., Pamme, N., Bienvenue, J., Eds.; The Printing House: Stoughton, WI, 2011, pp. 1758-1760.

Han et al., "Separation of long DNA molecules in a microfabricated entropic trap Array", *Science*, May 12, 2000; vol. 288, No. 5468, pp. 1026-1029.

Jo et al., "A single-molecule barcoding system using nanoslits for DNA analysis", *Proc. Natl. Acad. Sci.*, 2007, vol. 104, No. 8, pp. 2673-2678.

Kim et al., "A highly annotated whole-genome sequence of a Korean individual", *Nature*, 2009, vol. 460, pp. 1011-1015.

Kim et al., "Design and numerical simulation of a DNA electrophoretic stretching device", *Lab Chip*, 2007, vol. 7, pp. 213-225.

Kumar et al., "Origin of translocation barriers for polyelectrolyte chains", *J. Chem. Phys.* 2009, vol. 131, pp. 194903-1-194903-18.

Lam et al., "Genome mapping on nanochannel arrays for structural variation analysis and sequence assembly", *Nat. Biotech.*, Aug. 2012, vol. 30, No. 8, pp. 771-776.

Larson et al., "Single DNA molecule stretching in sudden mixed shear and elongational microflows", *Lab Chip*, 2006, vol. 6, Issue 9, pp. 1187-1199.

Levy et al., "DNA manipulation, sorting, and mapping in nanofluidic systems", Chem Soc Rev 2010; vol. 39, Issue 3, pp. 1133-1152.

Lim et al., "DNA methylation profiling in nanochannels", *Biomicrofluidics*, 2011, vol. 5, 034106, 9 pages.

Marie et al. "Nanofluidic devices towards single DNA molecule sequence mapping", *Journal of Biophotonics*, 2012, pp. 673-686, vol. 5, No. 8-9.

Mark et al., "Microfluidic lab-on-a-chip platforms: requirements, characteristics and applications", *Chem. Soc. Rev.*, 2010, vol. 39, pp. 1153-1182.

McCarroll et al., "Copy-number variation and association studies of human disease", *Nat. Genet.*, 2007, vol. 39, pp. S37-S42.

McCarthy et al., "Microduplications of 16p11.2 are associated with schizophrenia", *Nat. Genet.*, 2009, vol. 41, No. 11, pp. 1223-1227.

Menard et al., "A Device for Performing Lateral Conductance Measurements on Individual Double-Stranded DNA Molecules", *ACS Nano*, 2012, vol. 6(10), pp. 9087-9094.

Menard et al., "Electrokinetically-Driven Transport of DNA Through Focused Ion Beam Milled Nanofluidic Channels", *Anal. Chem.*, 2013, vol. 85, pp. 1146-1153.

Mills et al., "Mapping copy number variation by population-scale genome sequencing", *Nature*, 2011, vol. 470, pp. 59-65.

Perry et al., "Ion transport in nanofluidic funnels", *ACS Nano*, 2010, vol. 4, No. 7, pp. 3897-3902.

Pinard et al., "Assessment of whole genome amplification-induced bias through high-throughput, massively parallel whole genome sequencing", *BMC Genomics*, 2006, vol. 7, 216, 21 pages.

Pinkel et al., "Comparative genomic hybridization", *Annu. Rev. Genomics Hum. Genet.*, 2005, vol. 6, pp. 331-354.

Pinto et al., "Functional impact of global rare copy number variation in autism spectrum disorders", *Nature*, 2010, vol. 466, pp. 368-372.

Randall et al., "Methods to electrophoretically stretch DNA: microcontractions, gels, and hybrid gel-microcontraction devices", *Lab Chip*, 2006, vol. 6, pp. 516-525.

Reccius et al., "Conformation, length, and speed measurements of electrodynamically stretched DNA in nanochannels", *Biophys. J.*, Jul. 2008, vol. 95, pp. 273-286.

Reisner et al., "DNA confinement in nanochannels: physics and biological applications", *Rep. Prog. Phys.*, 2012, vol. 75, Issue 10, 106601, 35 pages.

Reisner et al., "Single-molecule denaturation mapping of DNA in nanofluidic channels", *Proc. Natl. Acad. Sci.*, Jul. 27, 2010; vol. 107, Issue 30, pp. 13294-13299.

Sebat et al., "Strong association of de novo copy number mutations with autism", *Science*, 2007, vol. 316, pp. 445-449.

Smith et al., "Overstretching B-DNA: The elastic response of individual double-stranded and single-stranded DNA molecules", *Science*, 1996, vol. 271, pp. 795-799.

Sorek et al., "Genome-wide experimental determination of barriers to horizontal gene transfer", *Science*, 2007, vol. 318, pp. 1449-1452.

Speicher et al., "Effect of genome-wide association studies, direct-to-consumer genetic testing, and high-speed sequencing technologies on predictive genetic counselling for cancer risk", *Lancet Oncol.*, Sep. 2010, vol. 11, pp. 890-898.

Stavis et al., "Nanofluidic structures with complex three-dimensional surfaces", *Nanotechnology*, 2009, vol. 20, Issue 16, 165302, 7 pages.

Stefansson et al., "Large recurrent microdeletions associated with schizophrenia", *Nature*, 2008, vol. 455, pp. 232-236.

Strychalski et al., "Non-planar nanofluidic devices for single molecule analysis fabricated using nanoglassblowing", *Nanotechnology*, 2008, vol. 19, Issue 16, 315301, 8 pages.

Teague et al., "High-resolution human genome structure by single-molecule analysis", *Proc. Natl. Acad. Sci.*, 2010, vol. 107, pp. 10848-10853.

Tegenfeldt et al., "The dynamics of genomic-length DNA molecules in 100-nm Channels", *Proc. Natl. Acad. Sci.*, Jul. 27, 2004; vol. 101, No. 30, pp. 10979-10983.

Topolancik et al., "Extraction and purification of genomic DNA via entrapment in an array of microposts", *Proceedings of the 15th International Conference on Miniaturized Systems for Chemistry and Life Sciences*, Oct. 2-6, 2011, Seattle, Washington; Landers, J. P., Herr, A., Juncker, D., Pamme, N., Bienvenue, J., Eds.; The Printing House: Stoughton, WI, 2011, p. 1026-1028.

Treangen et al., "Repetitive DNA and next-generation sequencing: computational challenges and solutions", *Nat. Rev. Genet.*, 2011, vol. 13, pp. 36-46.

Turner et al., "Confinement-induced entropic recoil of single DNA molecules in a nanofluidic structure", *Phys. Rev. Lett.*, 2002, vol. 88, 128103.

Utko et al., "Injection molded nanofluidic chips: Fabrication method and functional tests using single-molecule DNA experiments", *Lab Chip*, 2011, vol. 11, pp. 303-308.

Zangle et al., "Theory and experiments of concentration polarization and ion focusing at microchannel and nanochannel interfaces", Chem. Soc. Rev., 2010, vol. 39, pp. 1014-1035.

(56) References Cited

OTHER PUBLICATIONS

Zhou et al., "A single molecule system for whole genome analysis", *Perspectives in Bioanalysis, vol. 2, New High Throughput Technologies for DNA Sequencing and Genomics*; Mitchelson, K. R., Ed.; 2007, Elsevier: Amsterdam; pp. 265-300.

Zhou et al., "A whole-genome shotgun optical map of Yersinia pestis strain KIM", *Appl. Environ. Microbiol.*, 2002, vol. 68, No. 12, pp. 6321-6331.

Zhou et al., "Whole-genome shotgun optical mapping of Rhodobacter sphaeroides strain 2.4.1 and its use for whole-genome shotgun sequence assembly", *Genome Res.*, 2003, vol. 13, pp. 2142-2151.

Al et al. "Field Effect Regulation of DNA Translocation through a Nanopore" *Analytical Chemistry* 82(19):8217-8225 (2010).

Uba et al. "Nanogap Electrical Detection of Single Molecules Translocating Through a Nanochannel with Transverse Nanoelectrodes and Funnels Populated With an Array of Nanopillars" pp. 401-403, 15th International Conference on Miniaturized Systems for Chemistry and Life Sciences, Seattle, Washington, USA, Oct. 2-6, 2011.

Wu et al. "Complete plastic nanofluidic devices for DNA analysis via direct imprinting with polymer stamps" Lab on a Chip, 11(17):2984-2989 (2011).

Allison et al. "Direct atomic force microscope imaging of EcoRI endonuclease site specifically bound to plasmid DNA molecules" *Proceedings of the National Academy of Sciences, USA* 93:8826-8829 (1996).

Jo et al. "Elongation and Migration of Single DNA Molecules in Microchannels Using Oscillatory Shear Flows" *Lap Chip* 9(16):2348-2355 (2009).

Pang et al. "Fixed-Gap Tunnel Junction for Reading DNA Nucleotides" *ACS Nano* 8(12):11994-12003 (2014).

Viero et al. "Hydrodynamic Manipulation of DNA in Nanopost Arrays: Unhooking Dynamics and Size Separation" *Small* 7(24):3508-3518 (2011).

Wanunu, Meni "Nanopores: A journey towards DNA sequencing" *Physics of Life Reviews* 9:125-158 (2012).

Zhou et al. "Transport and Sensing in Nanofluidic Devices" *Annual Review of Analytical Chemistry* 4:321-341 (2011).

Zhu et al. "Arrays of horizontally-oriented mini-reservoirs generate steady microfluidic flows for continuous perfusion cell culture and gradient generation" *The Analyst* 129:1026-1031 (2004).

EPO machine translation of the Description section of JP 2005-241255, patented Sep. 8,2005, translation downloaded Dec. 15, 2020 (Year: 2005).

Evans, Christine E. "Direct On-Line Injection in Capillary Electrophoresis" Analytical Chemistry, 69:2952-2954 (1997).

Karlinsey, James M. "Sample introduction techniques for microchip electrophoresis: A review" Analytica Chimica Acta, 725:1-13 (2012).

\* cited by examiner

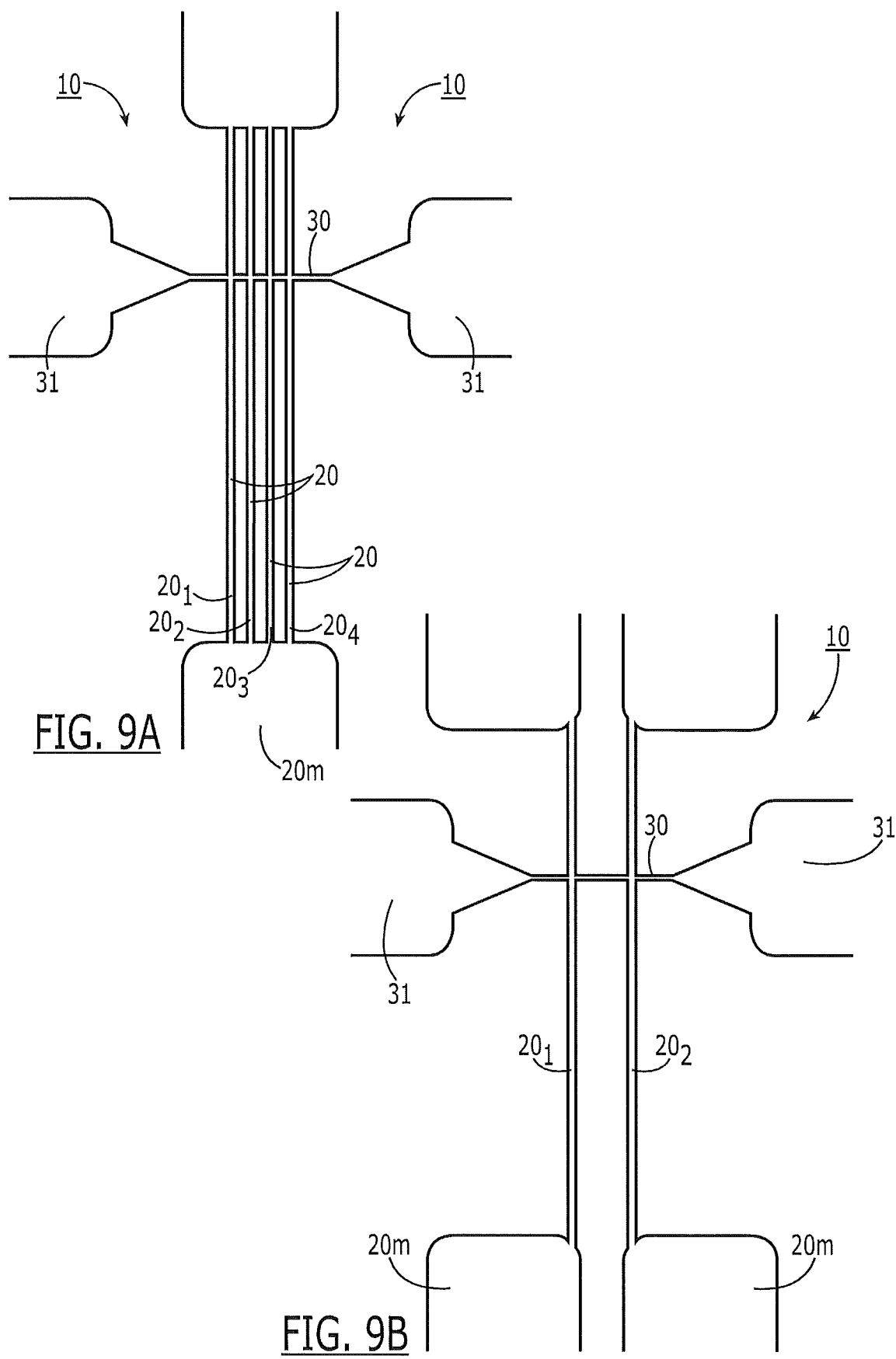

DEVICES WITH A FLUID TRANSPORT NANOCHANNEL INTERSECTED BY A FLUID SENSING NANOCHANNEL AND RELATED METHODS

RELATED APPLICATIONS

This application is a 35 USC § 371 national phase application of PCT/US2012/054128, International Filing Date Sep. 7, 2012, which claims the benefit of and priority to U.S. Provisional Application Ser. No. 61/533,523 filed Sep. 12, 2011, the contents of which are hereby incorporated by reference as if recited in full herein.

STATEMENT OF FEDERAL SUPPORT

This invention made with government support under Grant No. [[1- R01-]]HG002647 awarded by the National Institutes of Health. The United States government has certain rights in this the invention.

FIELD OF THE INVENTION

This invention relates to detection/characterization and/or measurement of molecules using fluidics and nanochannels.

BACKGROUND OF THE INVENTION

There has been considerable recent interest in the incorporation of nanoscale components in lab-on-a-chip fluidic devices. This interest owes its origin to several advantages (and differences that may be advantageously leveraged) in moving from the micron scale to the nanoscale. These differences include, for example, double-layer overlap (DLO) and its effect on electro-osmosis and charge permselectivity, localized enhancement of electric fields, higher surface to volume ratios, confinement effects on large synthetic and bio-polymers, and the emerging importance of entropic effects. See, e.g., Yuan et al., *Electrophoresis* 2007, 28, 595-610; Schoch et al., *Rev. Mod. Phys.* 2008, 80, 839-883; and Kovarik et al., *Anal. Chem.* 2009, 81, 7133-7140. Historic examples of nanoscale devices include the use of porous media and gels in chromatographic separations and filtration membranes with nanoscale pores. See, e.g., Lerman et al., *Biopolymers* 1982, 21, 995-997; and Tong et al., M. *Nano Lett.* 2004, 4, 283-287. Recent efforts, however, have been focused on engineering geometrically well-defined conduits for fluid and analyte transport and seamlessly integrating them into devices. See, e.g., Volkmuth et al., *Nature* 1992, 358, 600-602; and Striemer et al., *Nature* 2007, 445, 749-753. The advantage of such regular structures is the relative simplicity of pressure and field gradients, fluid flow, and molecular motion contained within, in contrast to these properties in more tortuous networks. The capability to define, characterize, and easily model these systems can allow a better understandings of separation mechanisms and single molecule physics, for example. See, e.g., Volkmuth et al., *Nature* 1992, 358, 600-602; Reisner et al., *Phys. Rev. Lett.* 2005, 94, 196101; and Salieb-Beugelaar et al., *Lab Chip* 2009, 9, 2508-2523.

Recently FIB milling techniques have been described to form nanofluidic devices. See, Menard et al., Fabrication of Sub-5 nm Nanochannels in Insulating Substrates Using Focused Ion Beam Milling, Nano Lett. 2011, 11, 512-517 (published Dec. 20, 2010); and U.S. Provisional Patent Application Ser. No. 61/384,738, filed Sep. 21, 2010, entitled, Methods, Systems And Devices For Forming Nanochannels, the contents of which are hereby incorporated by reference as if recited in full herein. In addition to FIB milling, a variety of other methods suitable for nanochannel fabrication can be used, including, for example, electron beam lithography, nanoimprint lithography, photolithography, templating or molding strategies, and other methods understood by one of ordinary skill in the art.

A number of nanofluidic devices have been proposed, including those with integrated miniature electrodes (nano- or micro-scale) for single-molecule sensing and/or nucleic acid sequencing. The incorporation of the electrodes as a device component can require difficult fabrications and small differences in electrode geometry may result in high device-to-device variability. In addition, fluorescent-based systems can have limited temporal resolution, typically about 400 frames or less per second, and may require relatively bulky and/or expensive optics and imaging components. There remains a need for alternate device designs and/or evaluation techniques.

SUMMARY OF EMBODIMENTS OF THE INVENTION

Embodiments of the invention provide substrates having at least one fluid transport nanochannel and at least one fluid sensing nanochannel that intersects the transport nanochannel.

The at least one sensing channel can be substantially orthogonal to the at least one fluid transport channel.

The at least one sensing channel can have a length that is less than that of the at least one fluid transport channel.

The at least one sensing channel can have a shorter length than the length of the transport channel, typically about 50% or less than a length of the at least one fluid transport channel.

The at least one sensing channel can have a width or depth dimension that is smaller than a corresponding dimension of the at least one fluid transport channel to inhibit analyte transport though the at least one sensing channel.

The substrate can include a cover plate that overlies the fluid transport and sensing channels and is sealably attached to the substrate.

The substrate can include a cover sealed to the substrate and a molecule of DNA in the at least one fluid transport nanochannel.

The at least one sensing channel can be a plurality of substantially parallel spaced apart sensing channels, each intersecting different portions of a respective one of the fluid transport channels.

The at least one fluid transport nanochannel can have a depth that is between about 1 nm to about 50 nm, and a width that is between about 1 nm to about 50 nm, and the at least one sensing channel has a depth that is between about 1-100 nm and a width that is between about 1-100 nm.

The substrate can include or be in communication with a first electrode and a second electrode, one residing on each side of a respective fluid transport nanochannel proximate a respective sensing channel.

The substrate can include or be in communication with a circuit configured to apply an ionic bias current across the sensing channel and monitor for a perturbation in the ionic current associated with an analyte in a respective fluid transport nanochannel passing the sensing channel.

Other embodiments of the invention are directed to devices for analyzing nucleic acids. The devices include a nanofluidic chip comprising at least one fluid transport nanochannel and at least one sensing nanochannel that intersects the at least one fluid transport channel.

The chip can include a substrate that at least partially defines the channels with a sealably attached cover.

The device can include an electric circuit that resides at least partially on the chip and/or is remote and in communication with the chip (e.g., all or some of the components of the circuit can reside on the chip or all or some of the circuit components can be remote from the chip) with a cooperating set of first and second spaced apart electrodes, one residing on each side of at least one of the flow transport channels proximate a respective end portion of a respective sensing channel.

The circuit can include a current source that applies a transverse bias current across the at least one sensing channel.

The circuit can be configured to provide data for evaluating molecular properties of the analyte, molecular identification and/or localized functionalization (molecular probe) mapping of an analyte in the fluid transport channel.

The circuit can be configured to simultaneously monitor the transverse current and image fluorescently labeled analyte molecules to thereby provide a complementary characterization of individual analyte molecules The device sensing channel can have a length that is less than the fluid transport channel, and the sensing channel can have at least one critical dimension that is less than a corresponding dimension of the fluid transport channel to thereby inhibit an analyte in the transport channel from entering the sensing channel.

The at least one fluid transport nanochannel comprises a single molecule DNA for analysis, and wherein at least one of the at least one sensing channel resides at a location away from a mouth of the at least one fluid transport nanochannel that allows the DNA molecule to be fully threaded therein.

The circuit can be configured to evaluate molecular properties of fluorescently labeled analytes simultaneously by imaging a respective fluorescent molecule and monitor perturbations in the transverse current.

Still other embodiments are directed to methods of analyzing an analyte. The methods include: (a) flowing an analyte through a transport nanochannel (e.g., via pressure or electrokinetics); and (b) monitoring for perturbation of a (transverse) bias current associated with the flowing step using a fluid sensing channel that intersects the transport nanochannel.

The method can also include simultaneous monitoring of the transverse current and imaging of fluorescently labeled analyte molecules. Such measurements can provide a complementary characterization of the individual analyte molecules.

The method can also include (c) determining molecular properties and/or identification of the analyte, length of the analyte or localized functionalization mapping based on data from the monitoring step.

The analyte can be or include a fluorescently labeled analyte molecule The method can include simultaneously imaging respective fluorescently labeled analyte molecules while monitoring perturbations to thereby provide a complementary characterization of individual analyte molecules.

Yet other embodiments are directed to methods of forming a fluidic analysis device. The methods include providing a substrate; and forming at least one fluidic transport nanochannel and at least one bisecting fluidic sensing nanochannel in the substrate. The fluidic sensing nanochannel can have at least one primary dimension that is smaller than at least one primary dimension of the at least one fluidic transport nanochannel.

In some embodiments, the substrate includes a thick overlayer and the method includes FIB milling the at least onebisecting channel through the overlayer into the substrate; then removing the overlayer to thereby form the fluidic sensing and transport nanochannels.

In other embodiments, the forming step is carried out using one or more of the following electron beam lithography, nanoimprint lithography, photolithography, templating or molding.

In some particular embodiments methods of forming the nanochannels can include: (a) providing a substrate having a thick overlayer; (b) FIB milling at least one (and optionally two or more) bisecting channels through the overlayer into the substrate; (c) removing the overlayer; and (d) forming at least one fluidic transport nanochannel and at least one bisecting fluidic sensing nanochannel in the substrate, the fluidic sensing nanochannel having at least one primary dimension that is smaller than at least one primary dimension of the at least one fluidic transport nanochannel, in response to the milling and removing steps.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIG. 5A is a low magnification image and FIG. 5B is a higher magnification image.

FIGS. 9A and 9B are top schematic views of devices with multiple transport channels using a sensing channel according to embodiments of the present invention.

DESCRIPTION OF EMBODIMENTS OF THE INVENTION

Figure 1:
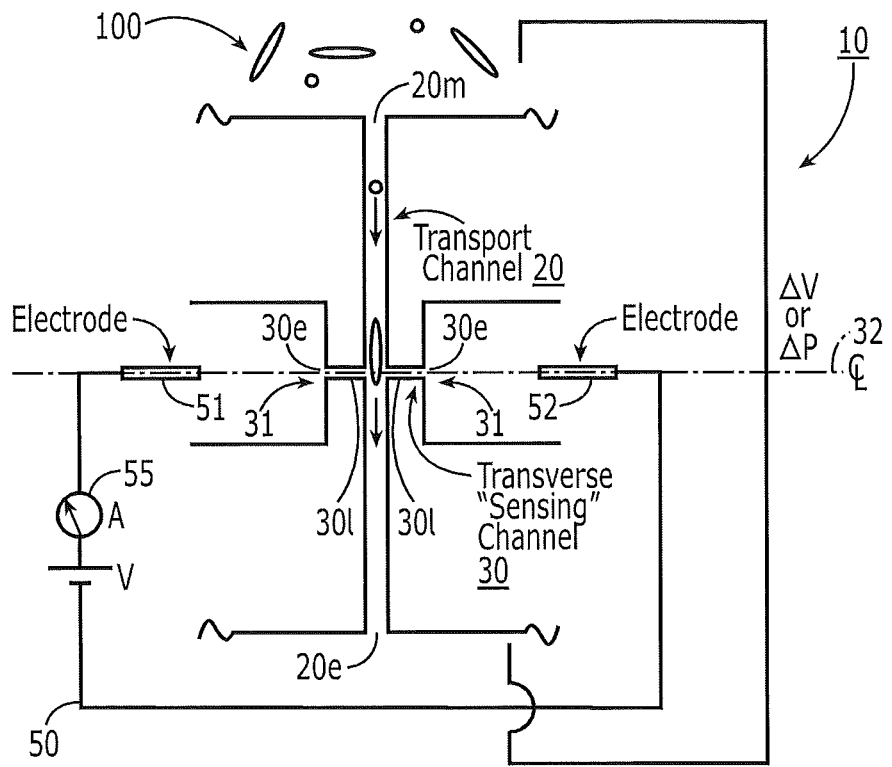
FIG. 1 is a schematic illustration of a device with bisecting fluidic channels according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. Well-known functions or constructions may not be described in detail for brevity and/or clarity.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The term "nanochannel" refers to a channel or trench having a critical dimension that is in a nanometer size. The nanochannel has sidewalls and a floor. The nanochannel can be formed into a solid substrate to have an open top surface and a closed bottom surface with the sidewalls extending therebetween. A cover may be used to seal or otherwise close the upper surface of the nanochannel(s). The term "primary dimension" refers to a width and/or depth dimension. The primary dimensions of a fluid transport nanochannel can be between about 1 nm to about 500 nm. The primary (also known as "critical") dimensions are both typically below about 100 nm, including between about 1-70 nm. In some embodiments, at least one primary dimension can be about 5 nm or less (on average or at a maxima).

The term "about" refers to parameters that can vary between +/−20% or less, such as +/−10%.

The term "sensing channel" refers to a fluidic channel, typically a fluidic nanochannel, that crosses over a respective fluid transport nanochannel. Electrical output, e.g., electrical data, such as conductance, from this laterally extending sensing channel can be monitored to provide data about the analyte in the fluid transport channel.

The term "fluid transport nanochannel" refers to a nanochannel that flows an analyte therethrough for analysis. The analyte can be any analyte of interest including, for example, single analyte molecules including synthetic and biological macromolecules, nanoparticles, small molecules, DNA, nucleic acids/polynucleic acids, peptides, proteins and the like. The transport through the nanochannel can be carried out using electrokinetics and/or pressure (forced pressure or pressure gradients) as is well known to those of skill in the art.

The term "circuit" refers to an entirely hardware embodiment or an embodiment combining software and hardware.

In some particular embodiments, the fluid transport nanochannels 20 (FIG. 1) can be defined as conduits having lengths substantially commensurate with, or exceeding, the analyte's contour length. If the nanochannel's width and depth are smaller than the radius of gyration of the macromolecule, then confinement of the molecule in the nanochannel necessarily results in molecular extension. The molecule's extended configuration will consist of a string of non-penetrating blobs (e.g., agglomerations) if the nanochannel width and depth are greater than the persistence length of the polymer (~50 nm for double-stranded DNA). Alternately, if the nanochannel critical dimensions are smaller than the persistence length, the molecule, unable to fold back on itself, can assume a reflecting rod conformation. In either case, the extension of a macromolecule along the length of a nanochannel facilitates single molecule characterizations. Specifically, the confinement of DNA in nanochannels has proven useful for sizing, mapping, separations, and epigenetic analysis.

FIG. 1 is a schematic illustration of a device 10 with at least one fluid transport nanochannel 20 and at least one sensing channel 30 that intersects the transport nanochannel 20. The transport channel 20 can be longer than the sensing channel 30. The transport channel 20 typically includes a mouth (entry) 20m for feeding a target analyte 100 and an exit end 20e. A voltage differential and/or pressure differential can exist between the mouth and exit 20m, 20e to drive/transport fluid flow of the analyte through the respective fluid transport channel 20 using pressure, capillary action and/or electrokinetics (positive/negative polarity) and the like.

As shown, the at least one sensing channel 30 can substantially orthogonally intersect the transport channel 20. However, slight angular offsets may also be used.

The sensing channel 30 can be symmetrically positioned with respect to the fluid transport channel 20 so that the fluid transport channel 20 bisects a respective sensing channel 30, e.g., each leg 30l of a respective sensing channel 30 has substantially the same length and primary dimensions (width×depth). However, in other embodiments, one leg 30l may be longer than the other and a width and/or depth dimension of one leg 30l may differ from another. The sensing channel 20 can have outer end portions 30e that are spaced apart a distance from the respective transport channel 20.

A circuit 50 can include a power source 55 that can electrically apply a transverse biasing current to the sensing channel 30. The end portions 30e can merge into a reservoir 31 that is configured to hold a flowable substance such as a fluid. The reservoir fluid can comprise an electrolyte solution, e.g., a high ionic strength electrolyte solution. The reservoir 31 and sensing channel 30 can comprise the same fluid as the transport channel 20, e.g., the same concentration of electrolyte solution or different concentrations of electrolyte solutions. Examples of suitable solutions include, but are not limited to, potassium chloride solutions in concentrations from about 35 mM to about 1 M. Alternatively, or additionally, a higher (or lower) ionic strength flowable material, liquid or solution can be used in the sensing channel 30, relative to the solution in the transport channel 20. Other fluid materials that can be used for a respective sensing channel 30 include amphiphilic electrolytes in organic solvents, electrolyte solutions in gels formed in the sensing channels, conducting polymers, ionic liquids, low melting temperature metals and alloys (e.g., "liquid metals"). Combinations of different flowable materials may also be used. In some embodiments where a transport channel 20 is intersected by more than one sensing channel 30, each sensing channel 30 may include a different flowable material or the same flowable material. In some embodiments, a respective sensing channel 30 has the same electrolyte solution as another sensing channel 30, at the same concentration or at different concentrations. In some embodiments, the fluid material can be converted to a solid or semi-solid material after introduction to the sensing channels. For example, gels can be cross-linked, polymers can be polymerized, and metals can be solidified by lowering the device operating temperature below the metal's melting point. In other embodiments, embedded electrodes can be grown in the sensing channels using plating or growth methods (e.g., electroplating or electroless plating of metals) known to one of ordinary skill in the art.

Figure 2:
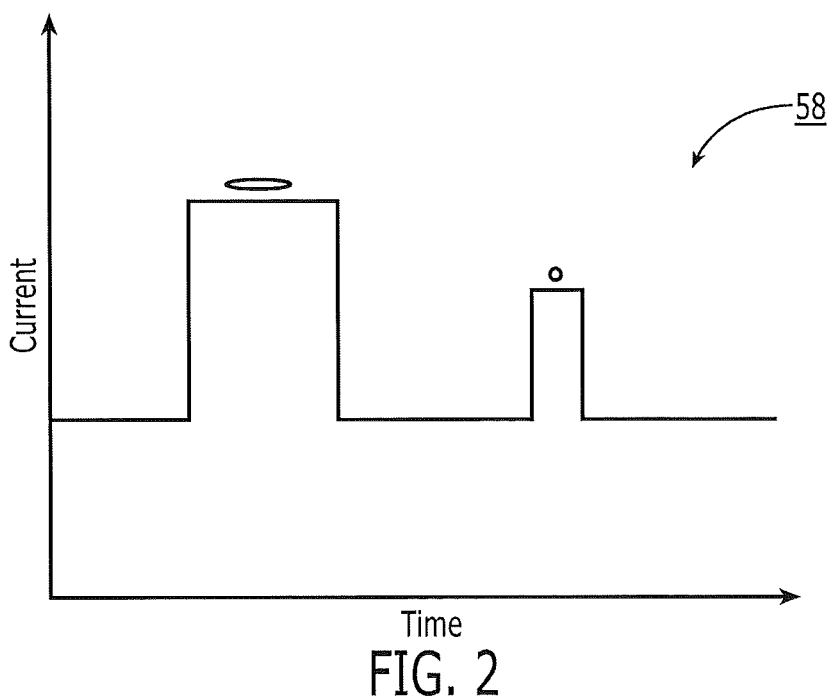
FIG. 2 is a graph of current versus time that can be detected by the device shown in FIG. 1 according to embodiments of the present invention.

The circuit 50 can include first and second electrodes 51, 52 that reside spaced apart from the end portions 30e of each leg 30l of a respective channel 30, one on each side of a respective transport channel 20. The electrodes 51, 52 may be substantially aligned with a centerline 32 of a respective sensing channel 30. The circuit 50 can include a power source 55 (e.g., a voltage source and/or current source) that can apply an ionic biasing current to the sensing channel 30. The circuit 50 can monitor ionic current perturbations 58 (FIG. 2) associated with the sensing channel 30, using, for example, one or more amplifiers (e.g., a patch clamp amplifier from Axon Instruments, Axopatch 200B) that is in communication with the sensing channel 30. The circuit 50 can include a processor and ammeter that can monitor for ionic current perturbations in the sensing channel 30 that is associated with an analyte in the transport channel 20 as it passes the sensing channel 30. Part or all of the circuit 50 can reside on the device 10 (e.g., chip or substrate) or part may reside in a remote device that is connected (wired or wirelessly) to the device 10. In some embodiments, the power source 55 can releasably engage the device 10.

Figure 14:
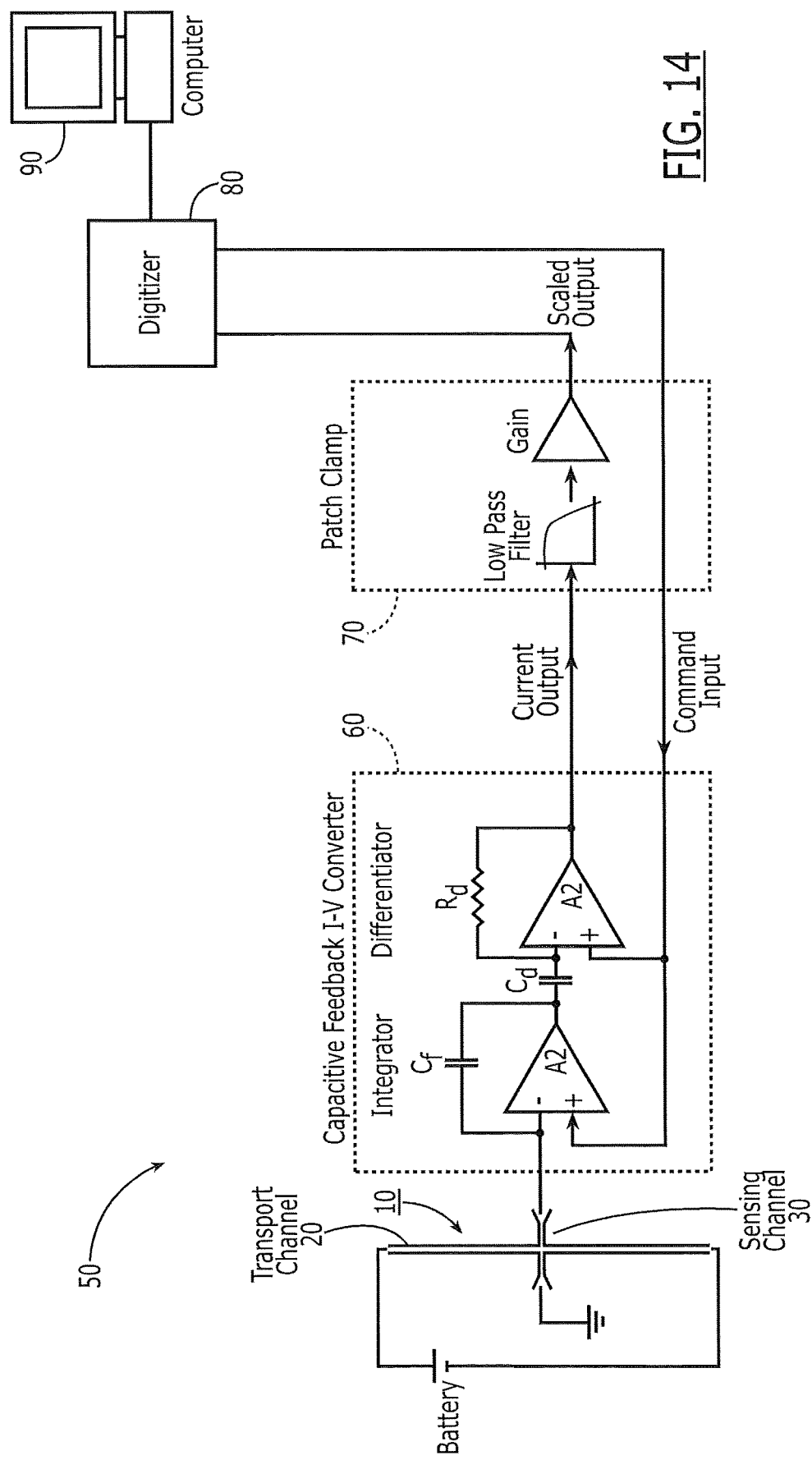
FIG. 14 is a circuit diagram of an exemplary circuit for operating a fluidic analysis device with a fluidic nanochannel transport channel and a fluidic sensing channel according to embodiments of the present invention.
Figure 15:
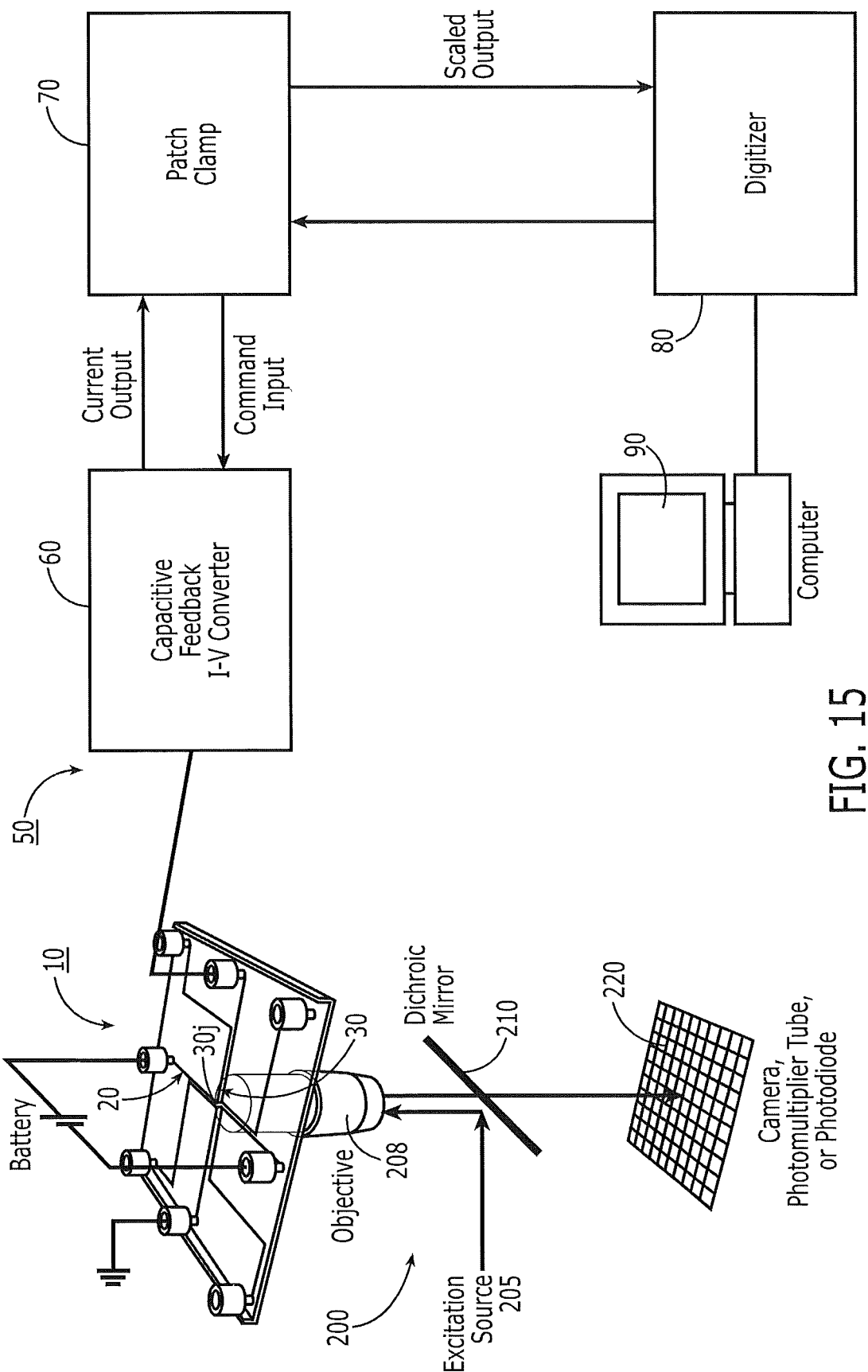
FIG. 15 is a circuit diagram of another exemplary circuit for operating a fluidic analysis device with the fluidic (transverse) sensing nanochannel and the fluidic transport channel according to embodiments of the present invention.

FIGS. 14 and 15 also illustrate examples of a circuit 50 that can be used to obtain the analysis data from the sensing channel 30 and that can analyze this data for the analyte in the transport channel 20 according to some particular embodiments of the present invention. The circuit 50 can include a capacitive feedback I-V converter 60, a patch clamp 70, a digitizer 80 and a computer 90 with a display. These components may be combined or be discrete components. FIG. 15 also illustrates that, in some embodiments, that the circuit 50 can include an imaging system 200 that can take a series of images of an analyte molecule in the flow channel 20 while the circuit 50 obtains current perturbation measurements from the sensing channel 30 (see, e.g., FIG. 11). The imaging system 200 can be any suitable imaging system. As shown, the system 200 can include an excitation light source 205 (typically for generating light that excites fluorescently labeled molecules), a mirror 210 and lens or other objective 208, and image generating device 220 such as one or more of a camera, photomultiplier tube or photodiode. The objective/lens 208 can reside under or over a primary surface of the device 10, shown as below. The electric inputs/outputs for the current sensing and flow operation can reside on an opposing side of the device 10, shown as on the upper side of the device 10. The device 10 may also be flipped to operate on its side (with the flat primary surfaces being upright or angled) rather than substantially horizontal as shown.

Figure 3:
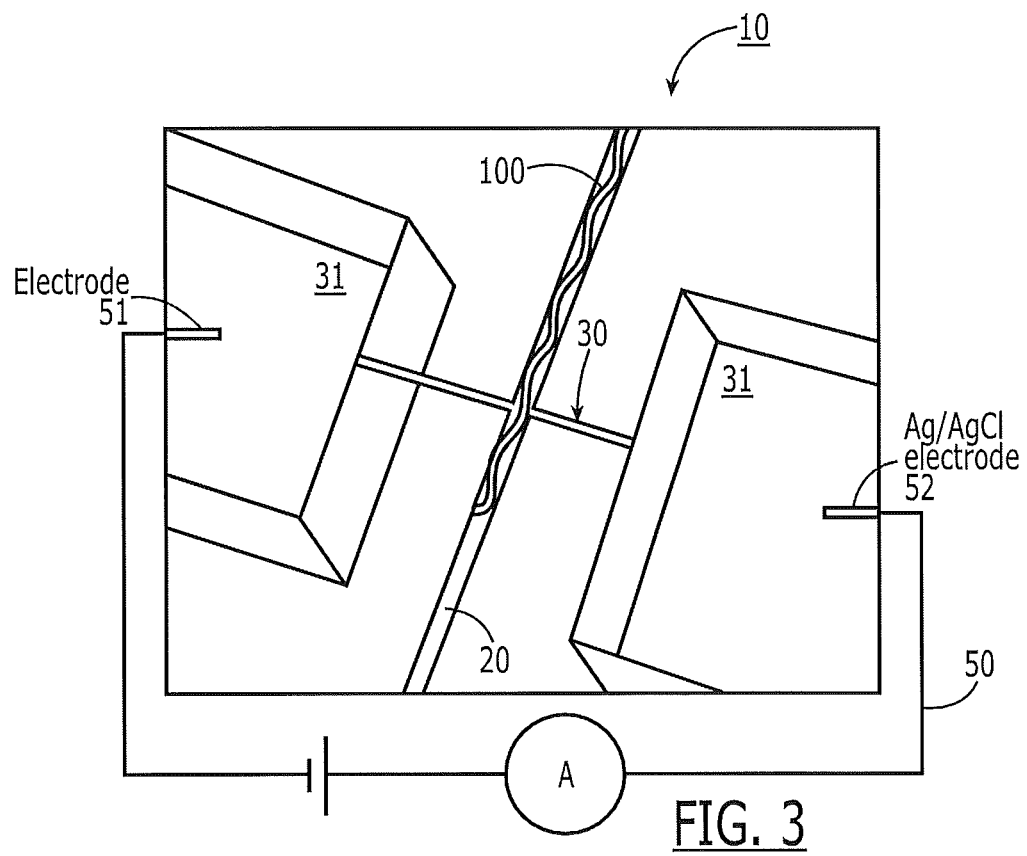
FIG. 3 is an enlarged illustration of a portion of the device shown in FIG. 1 proximate the fluidic junction of the cross-channel according to embodiments of the present invention.

FIG. 3 is an enlarged schematic view of a portion of the device 10 shown in FIG. 1, illustrating an analyte 100 in the flow transport channel 20 and lateral conductance sensing channel 30 with electrodes 51, 52 (e.g., Ag/AgCl electrodes) and circuit 50.

Figure 4:
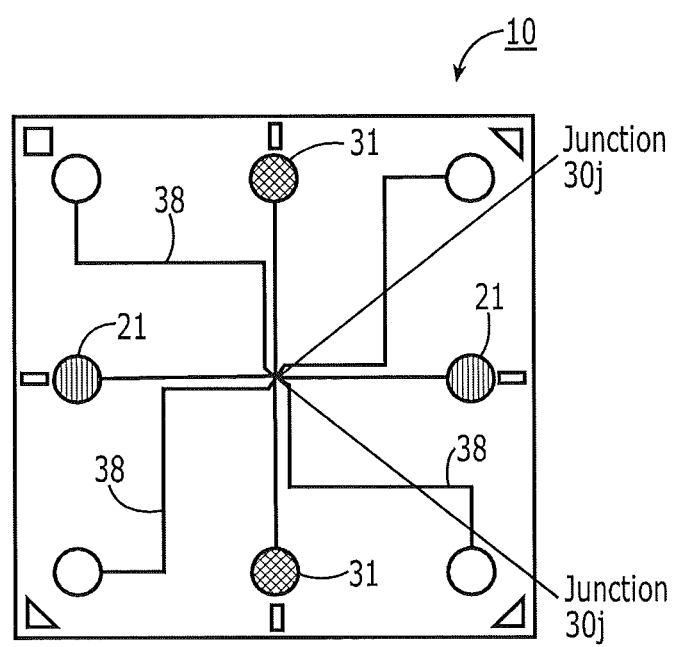
FIG. 4 is a schematic illustration of a device with at least one fluidic transport channel and at least one fluidic sensing channel and associated optional reservoirs, microchannels and electrical inputs according to embodiments of the present invention.

FIG. 4 is a schematic illustration of a device 10 with the junction 30j at the sensing channel 30 and transport channel 20 indicated. FIG. 4 also illustrates a compact "chip"-like device (about 25 mm×25 mm) showing the microchannels and associated reservoirs. The dark and cross-hatched reservoirs indicate where voltages can be applied. Transport is driven along the transport channel 20 by applying a bias across the solid dark reservoirs 21 and the voltage across the transverse (sensing) nanochannel is applied at the dashed/hatched reservoirs 31.

Figure 5:
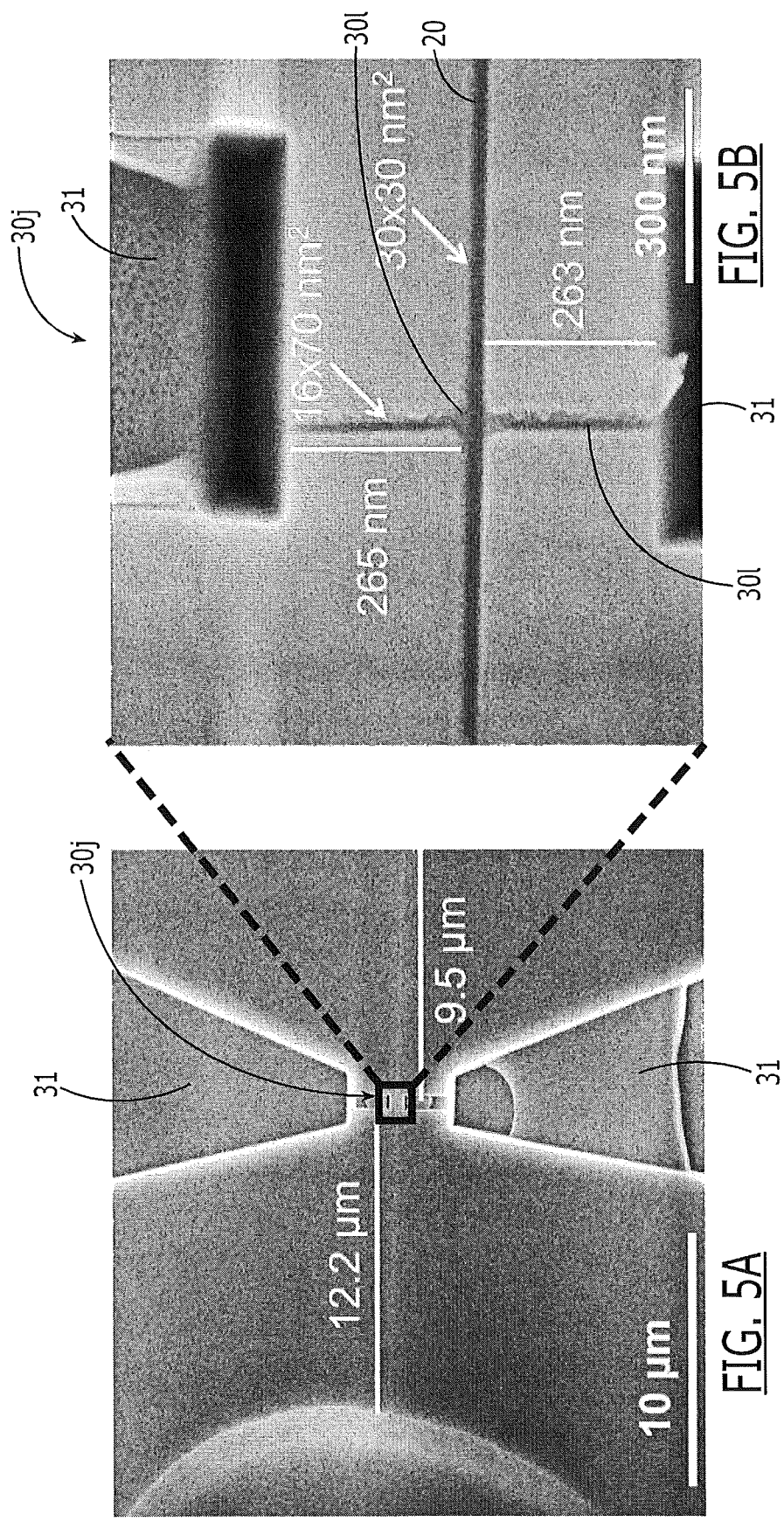
FIGS. 5A and 5B are scanning electron micrographs of a device with two bisecting nanofluidic channels according to some embodiments of the present invention.

An example of this junction 30j is shown greatly enlarged in FIGS. 5A and 5B. FIG. 5A illustrate scanning electron microscope (SEM) micrographs of the device 10. FIG. 5A is at low magnification (10 µm scale shown) and FIG. 5B shows this same junction 30j at higher magnification (300 nm scale shown). The length of the legs 30l of the sensing channel 30 is shown in this example at 265 nm and 263 nm, with primary (critical) dimensions at 16×70 nm² (width× depth). The transport channel 20 has a 30×30 nm² primary dimension configuration in this embodiment. FIG. 5A illustrates a position of the sensing channel 30 relative to the length of the transport channel 20 (about half-way-12.2 µm on one side and 9.5 µm on the other, in this example).

Figure 6:
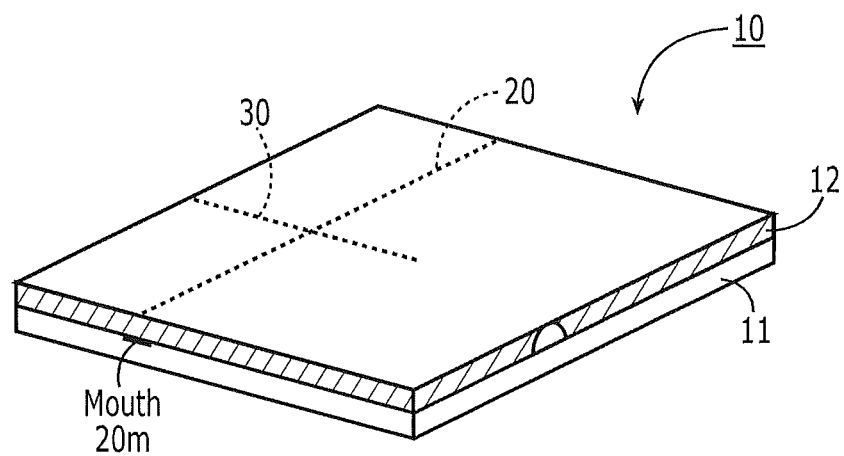
FIG. 6 is a side perspective illustration of a device with the bisecting channels shown in FIG. 1 provided as a substantially planar device with a sealed cover overlying a planar substrate holding the bisecting nanochannels according to some embodiments of the present invention.
Figure 7:
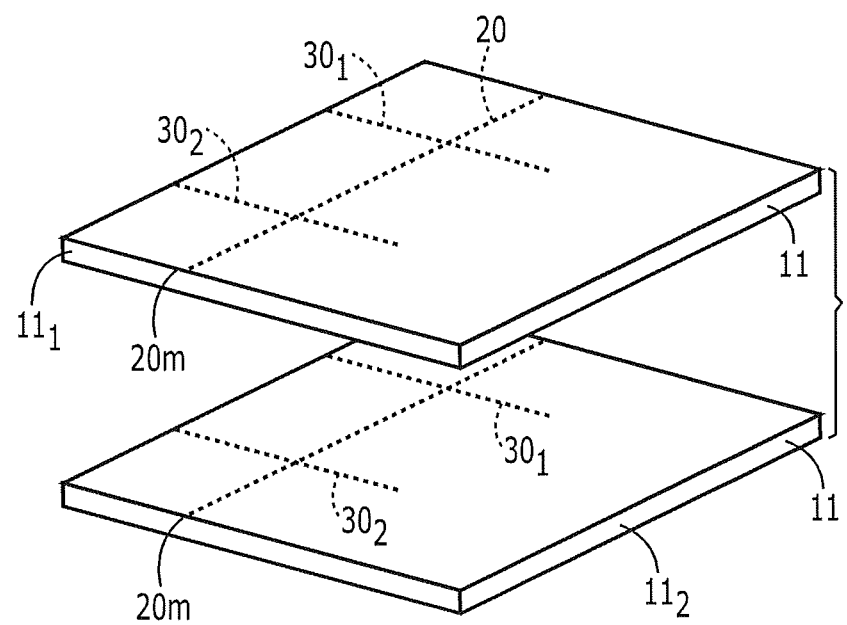
FIG. 7 is a side perspective illustration a multi-layer device with bisecting nanochannels according to some embodiments of the present invention.

The channels 20, 30 can be formed in a substantially planar substrate 11 as shown in FIGS. 6 and 7. A cover layer 12 can be sealed to the substrate 11 to define a fluid-tight seal. A fluid transport channel 20 can be substantially centered on the substrate, but can be off-center as well as shown in FIG. 6.

In particular embodiments, the nanochannels 20, 30 can be FIB milled using overlayers to control depth. Nanochannels can also be patterned using other techniques, such as electron beam lithography, nanoimprint lithography, photolithography, templating or molding strategies, and other methods understood by one of ordinary skill in the art.

Optionally, prior to and/or after formation of the nanochannels 20, 30 and removal of the overlayer 12, microchannels (FIG. 4) can be formed into the substrate to be in communication with one or more nanochannels 20, 30 using conventional techniques including, for example, FIB milling, photolithography or etching techniques. In some embodiments, the microchannels 38 can be formed using photolithographic patterning of a photoresist, followed by wet chemical etching. Photolithographically patterned channels may also be etched using dry etching techniques such as reactive ion etching (RIE) or deep reactive ion etching (DRIE). The larger channel features could also be formed using FIB milling procedures.

The substrate 11 can be hard (e.g., substantially rigid) or soft. The term "soft" refers to a material that is flexible, elastomeric, stretchable, plastic and/or polymeric. The substrate 11 can comprise a combination of hard and soft materials. The substrate 11 can be a substantially planar single layer of a monolithic material as shown in FIG. 6. The substrate 11 can be a substantially planar multi-layer structure with a plurality of laminated or otherwise securely attached stacked layers.

Examples of hard materials include, but are not limited to, substrates comprising one or combinations of: glass, quartz, silicon, and silicon nitride. The soft materials can have a low Young's Modulus value. For example, elastomers and harder plastics and/or polymers can have a range between about 0.1-3000 MPa. Examples of soft materials include, but are not limited to, polydimethylsiloxane (PDMS), polymethylmethacrylate (PMMA), and polyurethane.

Where soft (e.g., at least partially pliable or flexible) materials are used, the substrate 11 can be stretched during the milling step, then subsequently released to relax the substrate and reduce the channel width. The stretching can be carried out to stretch the material between about 10-30%, typically about 20%.

The devices 10 can be sealed with a glass or quartz cover 12 using fusion bonding or anodic bonding or using a PDMS-coated glass coverslip that reversibly seals the device (typically followed by heating to irreversibly seal the device). However, other formation techniques can be used, as well as other cover configurations/materials and/or seal types/processes.

FIG. 7 illustrates that the device 10 can comprise a plurality of stacked substrates 11, each with at least one transport channel 20 and at least one associated sensing channel 30. The cover 12 shown in FIG. 6 can be used in the device of FIG. 7. The upper substrate $11_1$ can define the cover for the lower substrate $11_2$ or each substrate $11_1$, $11_2$ can have its own cover 12 and the layers can be stacked to form a multi-layer fluidic analysis device 10. More than two substrates 11 can be used.

Figure 8A:
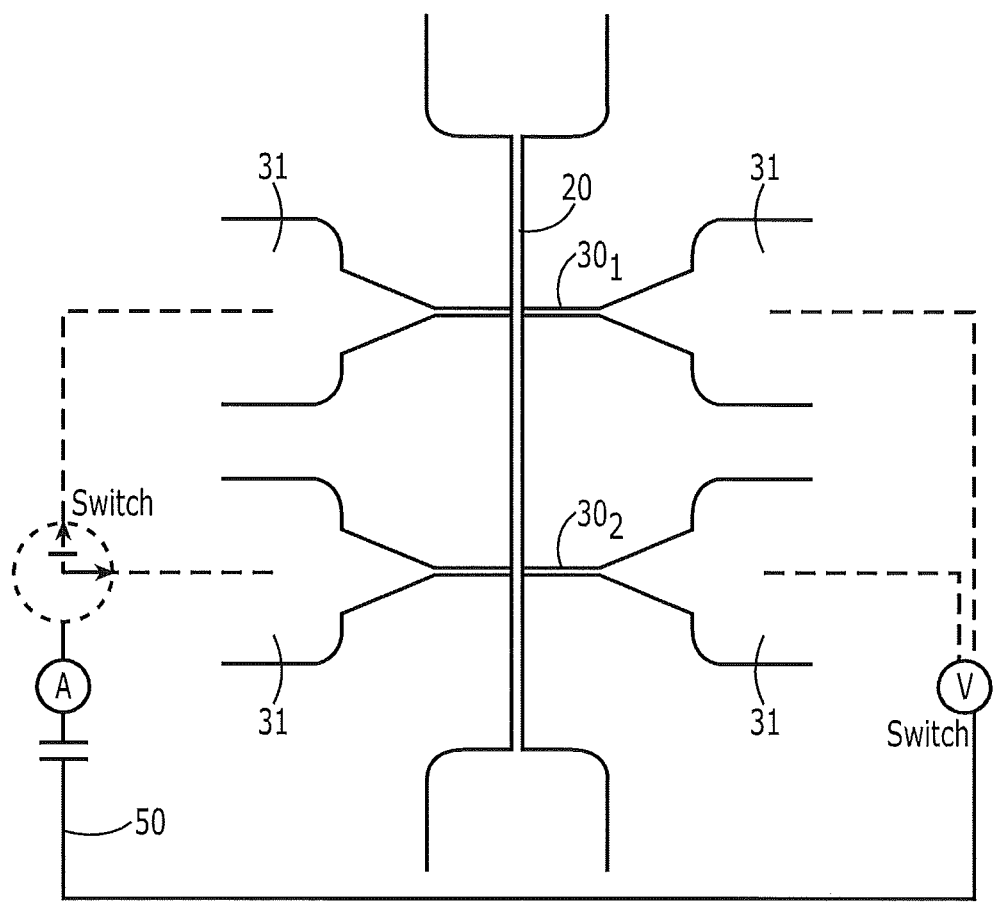
FIGS. 8A and 8B are top schematic views of devices with a plurality of sensing channels for a respective transport channel according to embodiments of the present invention.
Figure 8B:
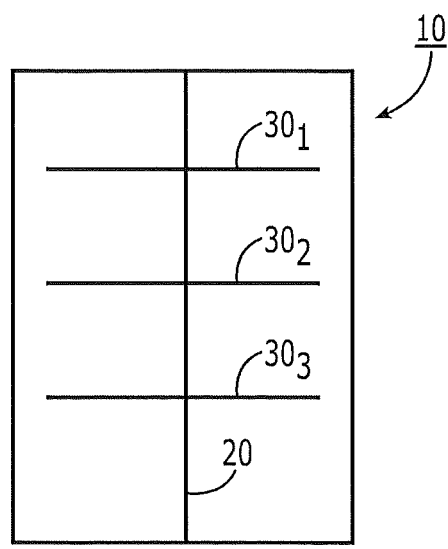

FIGS. 8A and 8B illustrate that the device 10 can include a plurality of spaced apart sensing channels 30 for a respective fluid transport channel 20. Although shown as two channels 30 in FIG. 8A and three in FIG. 8B, two, three, four, five or even more sensing channels 30 may be used. The channels $30_1$, $30_2$ may all be active (monitored) during use or one may be configured for use. Alternately, each of the different channels 30 can be selectively monitored or activated (at different times) during a particular analysis.

FIG. 8A also illustrates that the different sensing channels 30 may optionally be selectively addressed during operation using switches or the like. Alternately, a separate control/power circuit 50 can be used for each sensing channel $30_1$, $30_2$. The sensing channels $30_1$, $30_2$ can have the same configuration/length or different configurations and lengths.

The sensing channel can be selected based on the analyte being analyzed or the type of analysis desired. In some embodiments, each sensing channel 30 can be measured or monitored using a dedicated (different) amplifier/ammeter. In other embodiments, each channel 30 for a respective transport channel 20 can be selectively electrically connected using a programmable switch, for example, to a sensing channel, then the measurement data can be obtained using a shared amplifier/ammeter.

FIG. 8B illustrates three spaced apart sensing channels $30_1$, $30_2$, $30_3$, they may all have the same primary dimensions and length, or one or all may have a different length and/or primary dimension than another. The placement of the sensing channel 30 with respect to the transport channel 20 (at different positions along its length) and/or sensing channel size may reveal further electrical sensitivities. The sensing channels 30 may all be monitored during analysis or one or less than all may be activated/addressed during analysis operation. They may each have a common control circuit or dedicated circuits or share certain circuit components.

FIGS. 9A and 9B illustrate an embodiment with multiple transport channels 20, each in communication with one or more common sensing channels 30 (shown as one channel in this drawing, but additional sensing channels can be used). Thus, the same sensing channel 30 or channels $30_1$-$30n$ (where "n" is the upper number of different sensing channels, e.g., n=2-10) can be used for different transport channels $20_1$-$20n$ (typically, n=2-10). As shown in FIG. 9A, a common input port $20m$ can be used to feed the analyte or transport solution into respective transport channels 20. Although shown as four side by side parallel channels 20 ($20_1$-$20_4$), less than four (e.g., two or three) and more than four may be used.

FIG. 9B illustrates a device 10 with multiple individually addressable transport channels $20_1$, $20_2$. Each transport channel $20_1$, $20_2$ can include its own input port $20m$. In use, the device 10 can be operated so that only one transport channel 20 is active at any one time (e.g., the circuit 50 can be configured to drive molecules through one transport channel at a time). In other embodiments, the device 10 can be configured so that more than one transport channel 20 is active to drive molecules through concurrently.

Although FIG. 9B illustrates two transport channels $20_1$, $20_2$ sharing one sensing channel 30, more than two transport channels 20 may be provided and more than one sensing channel 30 may also be provided as discussed above.

The length of the fluid transport and sensing nanochannels 20, 30 can vary, typically according to end application. In some particular embodiments, the fluid transport nanochannels 20 can have a relatively short length such as about 100 nm, but more typically have a length between about 10 microns to 100 microns. In other embodiments, the fluid transport nanochannels 20 can be longer, such as between about 0.5-12 inches, although more typically between about 0.5 inches to about 2 inches.

The sensing channel 30 typically has a length dimension that is less than that of the fluid transport channel 20, such as, for example, at least about 50% less than the length of the fluid nanochannel 20, and in some embodiments between about 5% to about 20% of the length of the corresponding nanochannel 20, such as about 10%, about 11%, about 12%, about 13%, about 14%, about 15%, about 16%, about 17%, about 18%, and about 19%.

The sensing channel 30 can also, or alternatively, be configured to have a cross-section that is smaller than an analyte molecule's radius of gyration. In other embodiments, analyte translocation into the sensing channel 30 from the transport channel 20 may provide identifying information about the analyte. Thus, it is contemplated that the sensing channel 30 is not required to have primary dimensions that are smaller than the transport channel 20, and the analyte radius of gyration and the present invention should not be limited to any particular size (s).

Figure 10A:
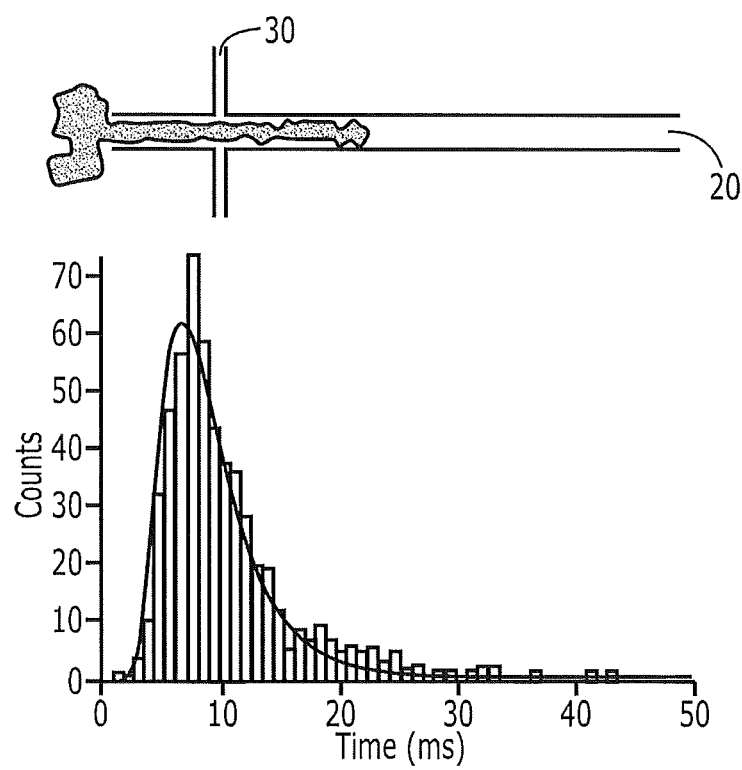
FIGS. 10A and 10B are schematic illustrations of sensing channel placement with respect to transport channel entry location and associated graphs of electrical output (counts versus time in ms) according to embodiments of the present invention.
Figure 10B:
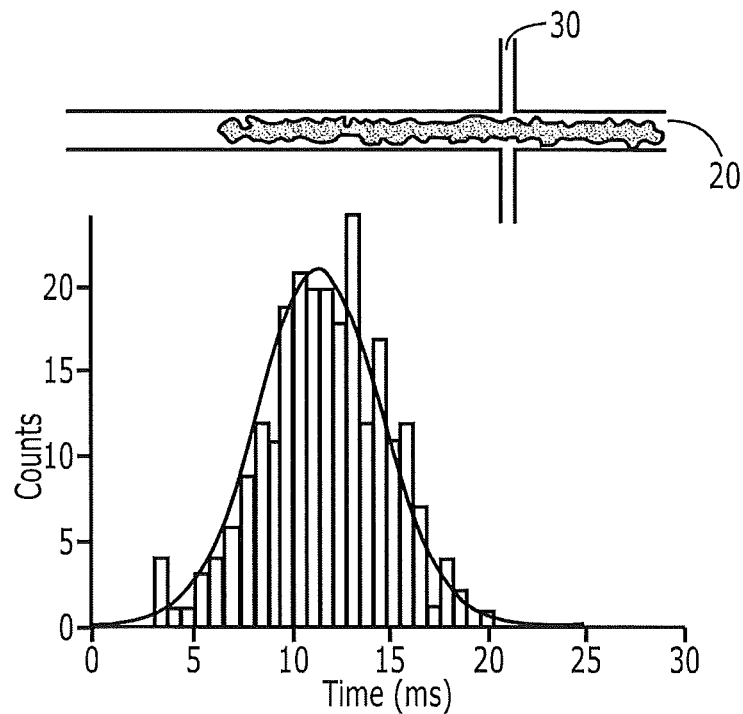

FIGS. 10a and 10b are graphs of distributions of event times shown with respect to two differently placed sensing channels 30 along a transport channel 20. FIG. 10(a) illustrates a transverse sensing nanochannel 30 located at a distance less than the extension length of λ-DNA from the transport channel mouth while FIG. 10(b) shows a transverse sensing nanochannel 30 located sufficiently far from the transport channel mouth that the DNA is fully threaded into the channel 20.

The transport channel 20 serves to confine single analyte molecules as they are being transported by an electric field or pressure gradient. The transverse sensing channel 30 is electrically biased and the ionic current monitored as analyte transport occurs. Transport of single analyte molecules past the channel intersection results in current perturbations. The frequency, amplitude, duration, and shape of these transient events as well as the profile of discrete sub-populations defined by these parameters can provide information on molecular properties such as size, charge, extension, concentration, and hydrophobicity. Mapping of molecular probe locations is also possible.

These crossed-channel devices 10 can serve as stand-alone sensors and analyzers or be integrated into lab-on-a-chip devices and/or with other functional components.

Figure 11:
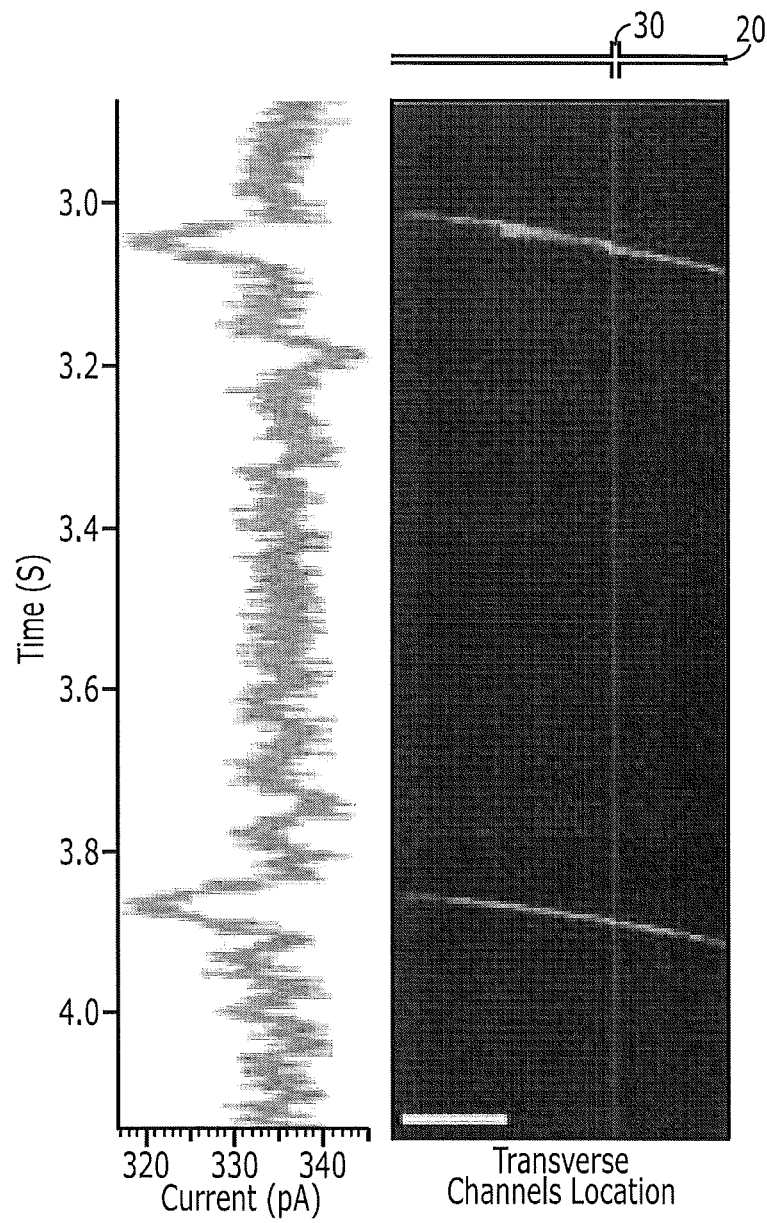
FIG. 11 is a graph of simultaneous electrical and optical detection of fluorescently stained DNA at time (s) versus current (pA) (left side) and a series of fluorescence images (right side) of a transport nanochannel (scale bar is 20 μm).

FIG. 11 illustrates simultaneous electrical and optical detection of two different fluorescently stained DNA molecules at a sensing nanochannel. The scale bar is 20 µm. The current across the sensing nanochannel vs. time is shown on the left and a series of fluorescence microscopy images of the transport nanochannel at the corresponding times are shown on the right. This confirms the current (pa) fluctuation corresponds to analyte passing the sensing channel. FIG. 11 also illustrates simultaneous electrical and optical detection of fluorescently stained DNA molecules at a sensing nanochannel 30 and confirms the current fluctuation corresponds to analyte passing the sensing channel. Of 326 events recorded in either the optical or electrical modes, 168 (52%) were simultaneously detected in the ionic conductance measurement and fluorescence images, confirming a single DNA molecule translocated past the transverse nanochannel. A number of translocation events (92, 28%) were observed optically, with no detectable conductance response. These were typically small DNA fragments. The prototype device may not be sufficiently sensitive to these fragments given the low ionic strength electrolyte solution. The remainder of events (66, 20%) were observed as ionic conductance perturbations with no corresponding optical event and may have been due to non-fluorescent species in the sample solution. These results illustrate how simultaneous fluorescence imaging can provide additional information useful for analyte characterization.

Embodiments of the invention can decouple the transport-driving electric field from that used for detection. Additionally, spatial resolution can be sensitive to the electric field across the bisected transverse sensing nanochannel and defined by its lateral extent, similar to the case of metal electrodes. Since the electrode/electrolyte interfaces are macroscopic and removed from the detection site, electrochemical processes are of little concern. Electrolyte solutions are poor conductors compared to metals. In addition, the volume of the region in which the two channels 20, 30 intersect at junction 30j, relative to the total volume of the sensing channel 30, can be made quite small. Despite these conditions, relatively large perturbations in the transverse ionic conductance can be observed/detected during driven DNA translocation. These transient current enhancements can be analyzed to determine electrophoretic mobilities of DNA through the transport nanochannels 20. In varying the location of the transverse sensing nanochannel 30 (relative to the entrance of the transport channel 20m) the distributions of event duration can differ for the cases in which DNA is fully confined within the nanochannel versus those in which DNA is in the process of threading. These and other factors may impact form factors and layouts of future sensing or sequencing devices containing either integrated metallic nanoelectrodes or nanofluidic channels 20, 30.

In some particular embodiments, the devices 10 can be formed using the methodology described in Menard et al., *Fabrication of Sub-5 nm Nanochannels in Insulating Substrates Using Focused Ion Beam Milling*, Nano Lett. 2011, 11, 512-517 (published Dec. 20, 2010); and U.S. Provisional Patent Application Ser. No. 61/384,738, filed Sep. 21, 2010, entitled, Methods, Systems And Devices For Forming Nanochannels, the contents of which are hereby incorporated by reference as if recited in full herein. That is, methods of forming a fluidic analysis device can include: (a) providing a substrate having a thick overlayer; (b) milling at least two bisecting channels through the overlayer into the substrate; (c) removing the overlayer; and (d) forming at least one fluidic transport nanochannel and at least one bisecting fluidic sensing nanochannel in the substrate in response to the milling and removing steps, such that the sensing channel has at least one primary dimension that is less than a primary dimension (e.g., width) of the transport channel and, typically, so that the sensing channel has a length that is less than about 50% that of the transport channel.

The term "thick" with reference to the overlayer means that the overlayer (e.g., the single or multi-layer structure) can have a thickness "TH" that is at least 50 nm, typically between about 50 nm to about 500 nm, and more typically between about 100 nm to about 400 nm. The overlayer can be a single monolithic material layer or may be a plurality of stacked attached layers. The overlayer can be conductive and configured to provide a desired low sputtering rate. The low sputtering rate is typically less than about 1.0 $\mu m^3/nC$, and more typically about 0.5 $\mu m^3/nC$ or less, such as, for example, about 0.10 $\mu m^3/nC$, about 0.23 $\mu m^3/nC$, and about 0.30 $\mu m^3/nC$. For a single monolithic overlayer structure, the overlayer can be metallic, such as a layer comprising aluminum. The overlayer can be configured so that it is non-reactive with the substrate upper surface.

While FIB milling is described for completeness and is believed to be particularly suitable for forming the nanochannels, other embodiments are directed to other forming techniques, as described above, including, for example, electron beam lithography, nanoimprint lithography, photolithography, templating or molding strategies, and other methods understood by one of ordinary skill in the art.

The present invention is explained in greater detail in the following non-limiting Examples.

EXAMPLES

Nanochannels were fabricated by focused ion beam (FIB) milling trenches in planar quartz substrates with widths and depths as small as 10 nm. To form fluidic nanochannels, the trenches were sealed by fusion bonding of a coverslip. Devices having sensing nanochannels located at different locations along the transport nanochannel were investigated. A series of experiments were performed in which λ-DNA was prepared in a 1 M KCl solution at concentrations of 0.25-5 µg/mL, and electrokinetically driven through the nanochannel. Ionic conductance through the transverse sensing nanochannel was measured with an Axopatch 200B patch clamp amplifier. In a series of similar experiments, λ-DNA was fluorescently stained with YOYO-1 intercalating dye to allow simultaneous optical and electrical monitoring. For the latter experiments, solutions were prepared in 125 mM KCl, a lower electrolyte concentration to maintain intercalation of the dye. Images of stained DNA passing sensing nanochannel were recorded at 100× magnification on an inverted microscope using a high gain CCD camera (Cascade II, Photometrics). The times at which electrical events occurred were compared to the times of corresponding optical events. The integrated intensity of fluorescence from each molecule of DNA was determined from the captured images and used as a measure of DNA size. A statistical analysis comparing the coincidence of optical and electrical measurements was performed.

Nanofluidic devices are capable of electrically monitoring the driven translocation of DNA molecules through a nanochannel using a long transport channel intersected by a shorter (e.g., orthogonal) sensing nanochannel. The ionic conductance of this transverse sensing nanochannel is monitored while DNA is electrokinetically-driven through the transport channel. When DNA passes the intersection, the transverse conductance is altered, resulting in a transient current response. In 1M KCl solutions this was found to be a current enhancement of 5-25%, relative to the baseline transverse ionic current. Two different device geometries were investigated (see Table 1 below). In one device, the DNA was detected after it was fully inserted into and translocating through the transport nanochannel. In the other device, the DNA was detected while it was in the process of threading into the nanochannel. It was found that these two conditions are characterized by different types of transport dynamics.

FIGS. 4, 5A and 5B show the general device architecture and representative micrographs of the nanochannel junction at different magnifications. The nanochannels are accessed by microchannels that are in turn accessed by ~100 µL reservoirs (FIG. 4). The transverse sensing nanochannels through which the ionic current is monitored are intentionally narrower than the transport channel. This creates an entropic barrier to DNA translocating through the orthogonal channel, making continued translocation through the long transport channel more favorable. The characteristic dimensions of the two devices used in these experiments are presented in Table 1. A significant difference between the two devices is the distance between the entrance of the transport channel and the intersection of the transport and transverse sensing nanochannels, 26.6 µm and 9.5 µm for Device A and Device B, respectively. The importance of these dimensions is discussed below.

The transport of double-stranded λ-phage DNA (48.5 kbp) was investigated, which has a contour length of 16.8 µm. In all experiments, the micro- and nanochannels were hydrodynamically filled with an electrolyte solution (1M KCl, 10 mM Tris, 1 mM EDTA). Solutions of λ-DNA (5 ng/µL) were prepared in this same electrolyte and then introduced via the microchannel accessing the entrance of the long transport nanochannel. The ionic current through the short transverse sensing nanochannel was driven and monitored using an Axopatch 200B patch clamp amplifier (Molecular Devices). A voltage of 50-200 mV was applied to macroscopic Ag/AgCl electrodes immersed in the appropriate reservoirs (hatch marked reservoirs 31 in FIG. 4). Single molecules of λ-DNA were electrokinetically-driven through the transport nanochannel by biasing platinum electrodes immersed in the reservoirs (blue solid dark reservoirs in FIG. 4). A floating power source was used to drive transport in these experiments with voltages of 4-10 V.

Figure 12A:
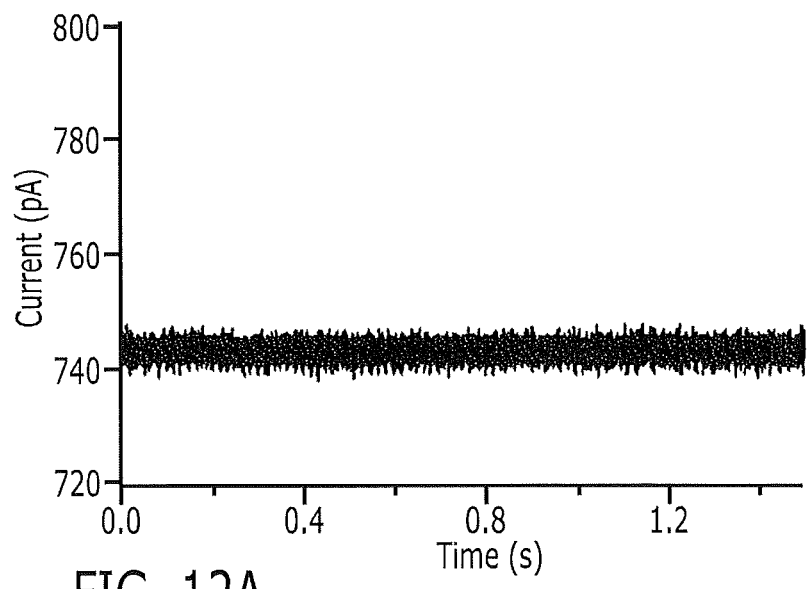
FIGS. 12a-12d are graphs of transverse ionic current measured in devices according to embodiments of the present invention (current pA versus time seconds).
Figure 12B:
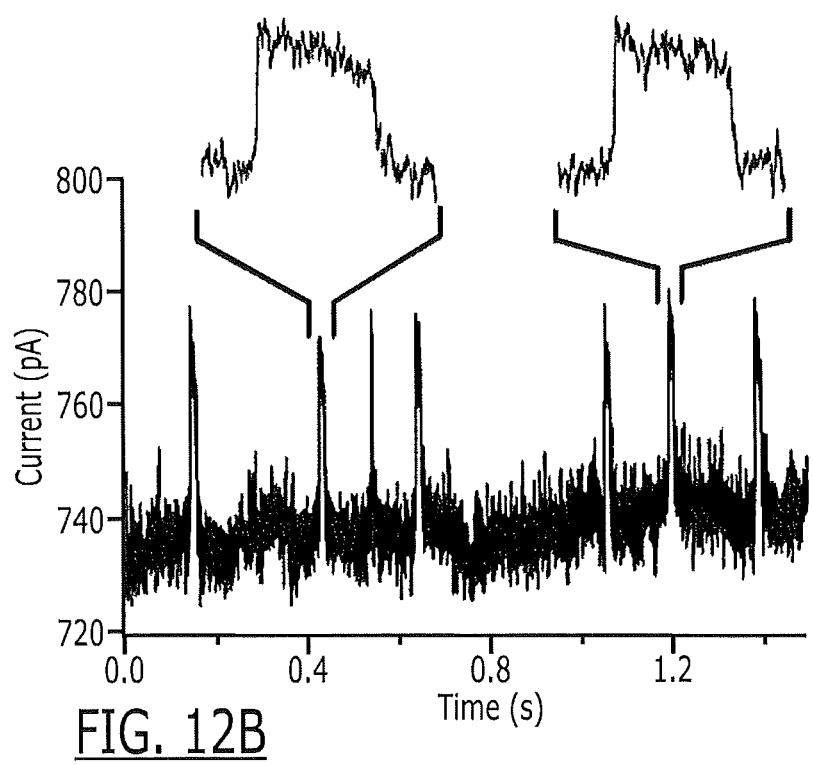

Upon applying the translocation-driving voltage across the transport nanochannel, current transients were observed through the transverse sensing nanochannel (FIGS. 12b, d). Various control experiments were performed in which the baseline transverse ionic current was measured in the absence of DNA (both with and without a voltage applied across the transport channel) or once DNA had been introduced to the device but in the absence of an applied bias across the transport channel (FIGS. 12a, c). In these cases, no transient events were observed. The most conspicuous characteristic of the current transients observed in both devices is their directionality. Current enhancements in a high-ionic-strength 1M KCl solution were observed. In nanopore experiments in which the current is measured axial to translocation, current reductions or enhancements are observed in high and low ionic strength solutions, respectively. In the case of the former, a reduced conductance is observed when DNA enters the pore due to the exclusion of the more mobile ions. In the latter case, the introduction of an elevated counterion concentration associated with the DNA actually enhances conductance. Curiously, we appear to observe an opposite effect.

Individual events were characterized on the basis of their amplitude and duration. These data for both devices is shown in FIG. 13. Similar to previous studies in both nanopores and nanochannels, a small number of events exhibiting multilevel current amplitudes were observed, consistent with folded DNA molecules. This population was quite small however (~5%) and the data analysis presented here was limited to single-level events. In Device A, the current amplitude of the transient events was 35±5 pA, or a 5% deviation from the baseline transverse current. The average event duration was 13±3 ms (0.27 μs/bp). From this event time, the electric field strength (820 V/cm), and the estimated extension length of the DNA molecules we can estimate the electrophoretic mobility of DNA in the 53×53 nm² transport nanochannels. The reflecting rod model of Odijk can be used to estimate the molecule's extension length, R:

$$R = L\left(1 - 0.085\left[\left(\frac{A}{P}\right)^{2/3} + \left(\frac{B}{P}\right)^{2/3}\right]\right), \quad \text{EQN (1)}$$

where L is the DNA contour length (16.8 μm), A and B are the nanochannel width and depth, respectively, and P is the persistence length (50 nm). The Odijk model is appropriate for nanochannels having critical dimensions much smaller than the persistence length. In reality, for nanochannels with the dimensions described, molecular conformations are likely transitioning between the blob model of de Gennes and the Odijk model. See, e.g., Odijk, T. *Phys. Rev. E* 2008, 77, 060901. However, these are steady-state models and it has been observed that the threading process initially extends the molecules beyond their equilibrium extension lengths. See, e.g., Mannion, J. T.; Reccius, C. H.; Cross, J. D.; Craighead, H. G. *Biophys. J.* 2006, 90, 4538. Given these considerations, extension lengths derived from the Odijk model offer a reasonable estimate for the length of DNA molecules passing the transverse sensing nanochannel. In the case of the transport nanochannel of Device A this corresponds to an extension length of 13.8 μm. The estimated electrophoretic mobility is therefore $1.3 \times 10^{-4}$ cm² V⁻¹ s⁻¹, consistent with literature values.

There are some significant differences apparent in the data collected from Device B. First of all, the current amplitude of the transient events is 271±53 pA, or ~27% of the baseline ionic current. The relatively low conductance of the ionic solution in the transverse sensing nanochannel results in significant resistances in series with the region of the nanochannel sensitive to DNA-induced perturbations (i.e. the intersection of the transport and transverse sensing nanochannels). As a result, given the comparable cross-sections of the transverse sensing nanochannels in these two devices, this five-fold greater sensitivity in Device B is commensurate with the 77% shorter transverse sensing nanochannel in this device. The distribution of event times observed in Device B is distinct from that of Device A in that it is significantly skewed and better characterized as a lognormal distribution. The extension length estimated using the Odijk model in the 31×28 nm² transport nanochannel is 14.8 μm. This is longer than the distance from the transport nanochannel entrance to the intersection of the transport and transverse sensing nanochannels (9.5 μm). In other words, λ-DNA molecules are still undergoing the threading process as the leading edge of the molecules are reaching the point of detection. Their velocity is therefore affected by threading mechanics that are a function of initial molecular configurations. Event time distributions are often skewed in nanopore experiments where molecular threading is a main component of the DNA translocation process. This is in contrast to event distributions in devices where measurements are made on DNA molecules that are fully inserted into the nanochannels, which strongly limits the distribution of conformations. From the estimated extension length, most probable event time (16 ms), and electric field strength (1470 V/cm) we estimate an electrophoretic mobility of $0.6 \times 10^{-4}$ cm² V⁻¹ s⁻¹. A lower mobility in smaller nanochannels is not surprising given the larger contribution of DNA/wall interactions. A measure of caution is warranted in more quantitative comparisons, however, given the uncertainty in the λ-DNA extension lengths used for these calculations. Nonetheless, the values for DNA electrophoretic mobility determined from these studies are consistent with previously reported values.

Finally, it may be desirable to use devices in which the transverse sensing nanochannel or nanoelectrodes are located at various positions along the transport channel, depending on the desired operating conditions. The greater tension on the DNA molecule, resisted by the hydrodynamic drag of the unthreaded portion of the molecule, will result in greater extension and lower velocity during the threading process. Thus, a transverse sensing nanochannel or electrode located near the entrance of the transport channel may enable conductance measurements with greater spatial and temporal resolution. In cases where the transverse sensing nanochannel or electrode is located far from the transport channel entrance, and the DNA is fully threaded, a constant velocity is expected as each segment of the molecule experiences equivalent Lorentz and drag forces. Such conditions may facilitate DNA sizing, mapping, and sequencing.

The transport of single λ-DNA molecules were observed as transient current enhancements in high ionic strength electrolyte solutions. The duration of these stochastic transient signals were analyzed to estimate the electrophoretic mobility of DNA in the transport nanochannels. It was observed that the shapes of the event time distributions are dependent upon the location of the transverse sensing region relative to the transport nanochannel entrance.

TABLE 1

Nanochannel Dimensions in Lateral Conductance Devices

| device | transport nanochannel | | | distance, entrance to cross | transverse nanochannel | | |
|---|---|---|---|---|---|---|---|
| | width | depth | total length | | width | depth | total length |
| A | 53 nm | 53 nm | 50.4 µm | 26.6 µm | 25 nm | 43 nm | 2.2 µm |
| B | 31 nm | 28 nm | 21.7 µm | 9.5 µm | 22 nm | 59 nm | 0.5 µm |

Figure 12C:
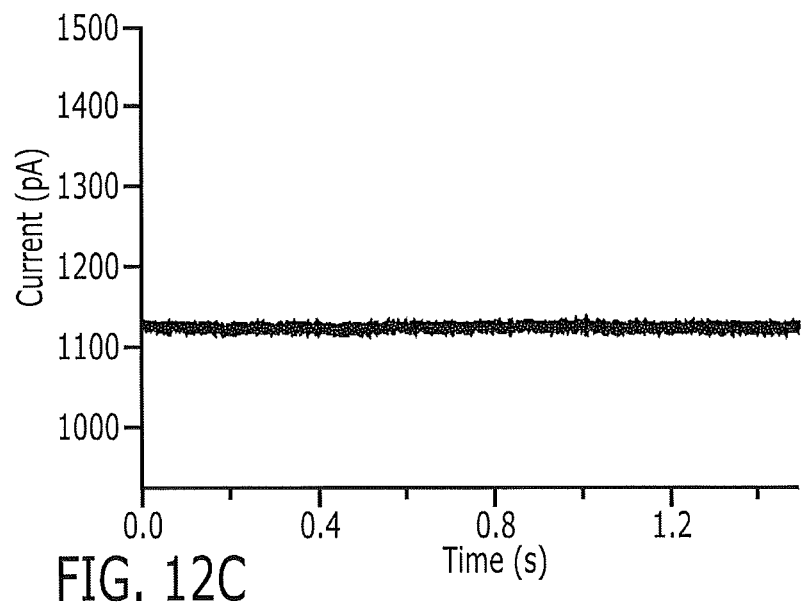
Figure 12D:
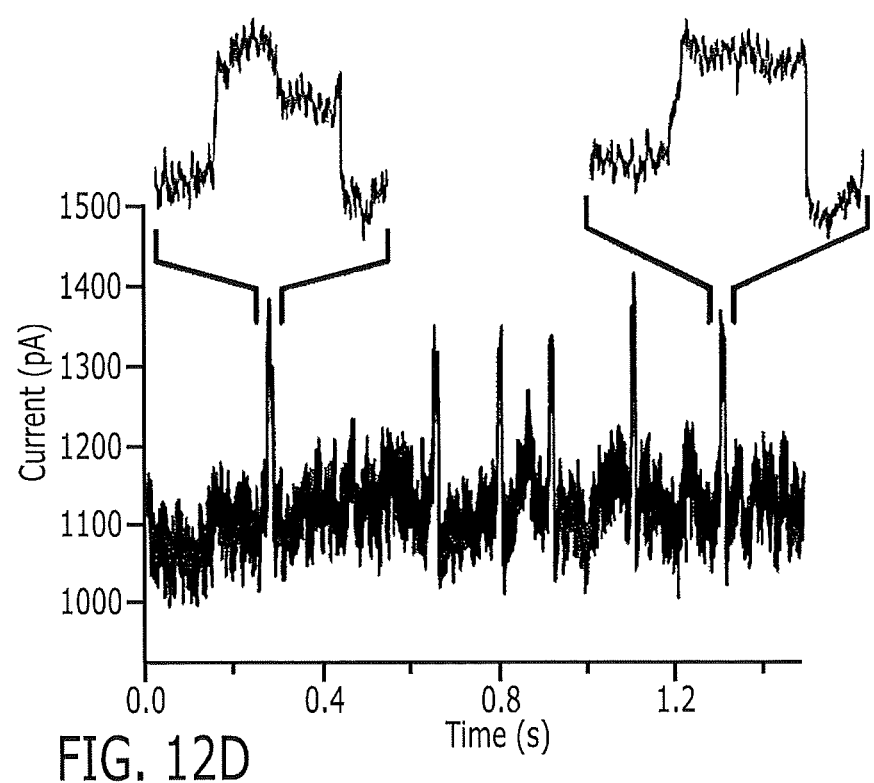

FIGS. 12a-12d illustrate measured ionic current of Device A/B. FIG. 12a shows transverse ionic current measured in Device A (Table 1) when DNA was not being driven through the transport channel (50 mV applied). FIG. 12(b) shows transverse ionic current in Device A detecting electrokinetically-driven DNA transport. FIG. 12(c) shows transverse ionic current measured in Device B when DNA was not being driven through the transport channel (100 mV applied). FIG. 12(d) shows transverse ionic current measured in Device B when a voltage was applied across the transport channel, driving DNA translocations. The left hand inset in FIG. 12(d) shows a relatively rare multilevel event consistent with DNA translocating in a folded state.

Figure 13A:
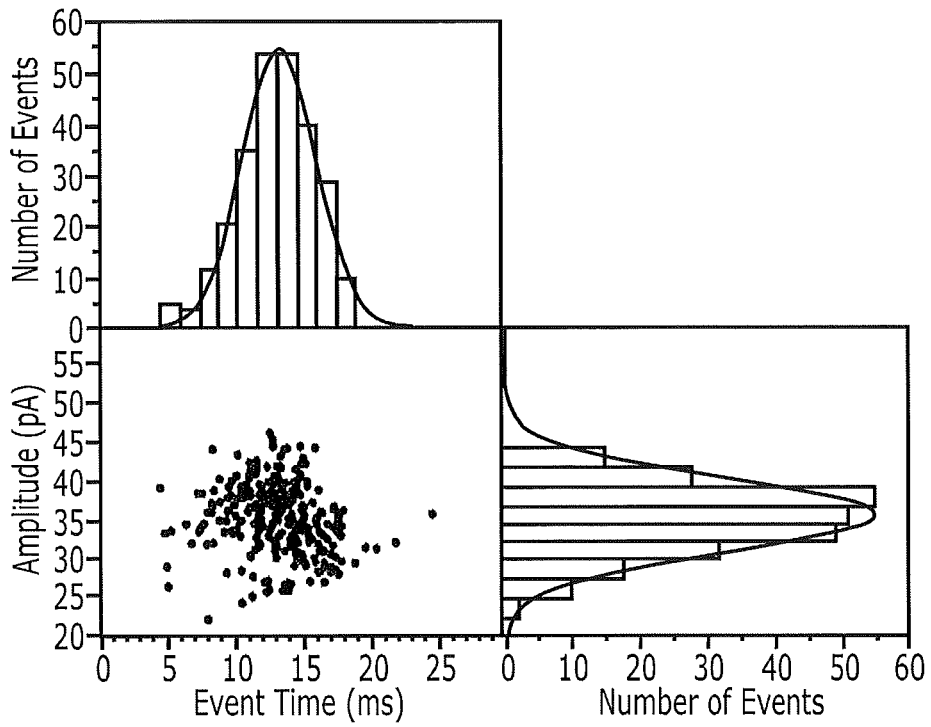
FIGS. 13a and 13b are event time (ms) and current amplitude (pA) histograms and scatter plots for different devices with bisecting fluidic nanochannels according to embodiments of the present invention.
Figure 13B:
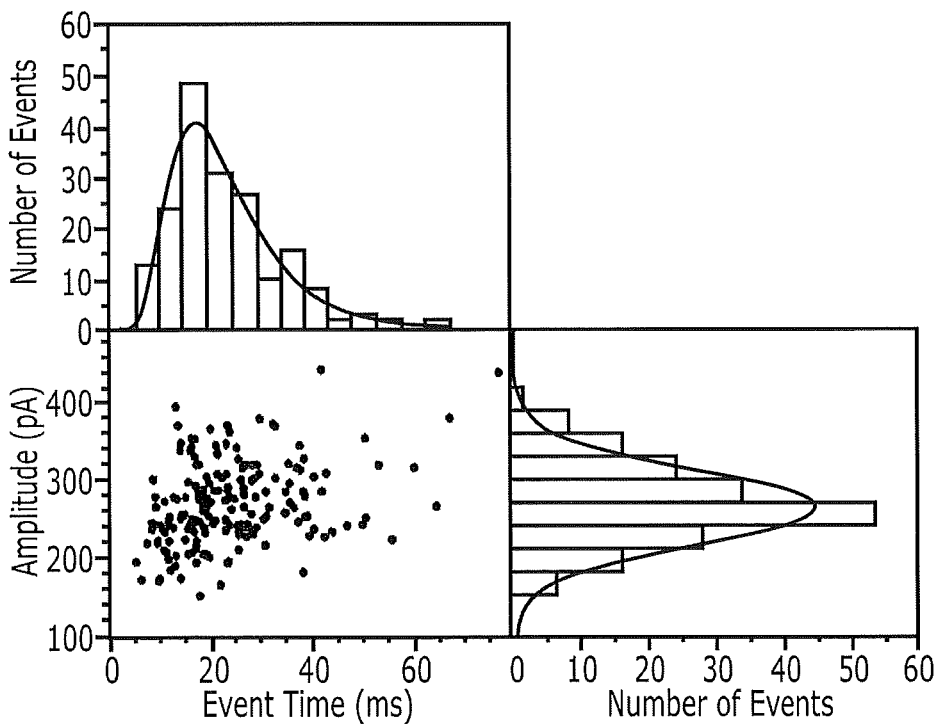

FIGS. 13a-b are event time and current amplitude histograms and scatter plots. FIG. 13a shows the data for Device A (Table 1) and FIG. 13(b) shows the data for Device B (Table 1). All of the histograms were fit with normal distributions with the exception of that for event times measured in Device B, which was fit to a lognormal distribution.

Nanofluidic implementations with nanochannels are well-suited for a number of applications including single molecule detection and identification, confinement and manipulation of biopolymers, biological assays, restriction mapping of polynucleotides, DNA sizing, physical methods of genomic sequencing, and fundamental studies of the physics of confinement.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A substrate comprising:
   at least one fluid transport nanochannel;
   at least one fluid sensing nanochannel that intersects the fluid transport nanochannel at an intersection between inlet and outlet ends of the at least one fluid transport nanochannel;
   at least one pair of first and second opposite electrodes, one residing on each side of a respective fluid transport nanochannel proximate a respective sensing nanochannel;
   at least one pair of third and fourth opposite electrodes, at least one residing adjacent to each of inlet and outlet ends of the at least one fluid transport nanochannel; and
   a circuit residing at least partially on the substrate and/or is in communication with the substrate, wherein the circuit comprises a first power source connected to the at least one pair of first and second opposite electrodes, wherein the first power source and the at least one pair of first and second opposite electrodes cooperate to apply a voltage transverse to a direction of fluid and/or analyte transport of an analyte in the respective fluid transport nanochannel,
   a second floating power source, electrically decoupled from the first power source and connected to the at least one pair of third and fourth opposite electrodes, wherein the second floating power source and the at least one pair of third and fourth opposite electrodes cooperate to apply a voltage along the respective fluid transport nanochannel to drive the analyte through the respective fluid transport nanochannel; and
   a processor programmed to measure via an ammeter an electrical output from the respective fluid sensing nanochannel, and the measured electrical output provides data about the analyte present at the intersection in the at least one fluid transport nanochannel.

2. The substrate of claim 1, wherein the at least one sensing nanochannel is substantially orthogonal to the at least one fluid transport nanochannel.

3. The substrate of claim 1, wherein the at least one sensing nanochannel has a length that is less than a length of the at least one fluid transport nanochannel.

4. The substrate of claim 1, wherein the at least one sensing nanochannel has a length that is about 50% or less than that of the at least one fluid transport nanochannel.

5. The substrate of claim 1, wherein the at least one sensing nanochannel has a width or depth dimension that is smaller than a corresponding dimension of the at least one fluid transport nanochannel to inhibit analyte transport through though the at least one sensing nanochannel.

6. The substrate of claim 1, further comprising a cover plate that overlies the fluid transport and sensing nanochannels and is sealably attached to the substrate.

7. The substrate of claim 1, further comprising a cover sealed to the substrate and a molecule of DNA as the analyte in the at least one fluid transport nanochannel.

8. The substrate of claim 1, wherein the at least one sensing nanochannel is a plurality of substantially parallel spaced apart sensing nanochannels, each intersecting a different portion of a respective one of the at least one fluid transport nanochannel.

9. The substrate of claim 1, wherein the at least one fluid transport nanochannel has a depth that is between about 1 nm to about 50 nm, and a width that is between about 1 nm to about 50 nm, and wherein the at least one sensing nanochannel has a depth that is between about 10-100 nm and a width that is between about 10-100 nm.

10. The substrate of claim 1, wherein the electrical output measured is a perturbation in a transverse ionic current from the at least one fluid transport nanochannel solely due to the analyte passing through the intersection.

11. A device for analyzing an analyte, comprising:
   a nanofluidic chip comprising at least one fluid transport nanochannel and at least one fluid sensing nanochannel that intersects the at least one fluid transport nanochannel at an intersection between inlet and outlet ends of the at least one fluid transport nanochannel, at least one pair of first and second opposite electrodes, one residing on each side of a respective fluid transport nanochannel proximate a respective sensing nanochannel, and at least one pair of third and fourth opposite electrodes, at least one residing adjacent to each of inlet and outlet ends of the at least one fluid transport nanochannel;

a circuit residing at least partially on the chip and/or in communication with the chip, wherein the circuit comprises a first power source, a processor, and an ammeter, wherein the first power source is connected to the at least one pair of first and second opposite electrodes, wherein the first power source and the at least one pair of first and second opposite electrodes cooperate to apply a voltage transverse to a direction of fluid and/or analyte transport of the respective analyte in the respective fluid transport nanochannel; and a second floating power source that is electrically decoupled from the first power source and is connected to the at least one pair of third and fourth opposite electrodes, wherein the second floating power source and the at least one pair of third and fourth opposite electrodes cooperate to apply a voltage along the respective transport nanochannel to drive the respective analyte through the respective transport nanochannel, wherein the processor is programmed to measure via the ammeter an electrical output from the respective fluid sensing nanochannel, and wherein the electrical output measured provides data about an analyte present at the intersection in the at least one fluid transport nanochannel.

12. The device of claim 11, wherein the chip comprises a substrate that at least partially defines the at least one fluid transport nanochannel and the at least one fluid sensing nanochannel, the chip further comprising a sealably attached cover that defines a ceiling or floor for the at least one fluid transport nanochannel and the at least one fluid sensing nanochannel.

13. The device of claim 11, wherein the electrical output measured is a perturbation in a transverse ionic current from the respective fluid transport nanochannel solely due to the analyte passing through the intersection.

14. The device of claim 11, wherein the electrical output measured provides the data to evaluate molecular properties of the analyte, and/or provides molecular identification and/or localized functionalization (molecular probe) mapping of the analyte in the at least one fluid transport nanochannel.

15. The device of claim 13, further comprising an image generation system in communication with the chip configured to obtain a series of images to evaluate molecular properties of one or more fluorescently labeled analytes as the analyte in the at least one fluid transport nanochannel while simultaneously detecting the perturbation in the transverse ionic current.

16. The device of claim 11, wherein the at least one sensing nanochannel has a length that is less than the at least one fluid transport nanochannel, and wherein the at least one sensing nanochannel has at least one critical dimension that is less than a corresponding dimension of the at least one fluid transport nanochannel to thereby inhibit the analyte in the respective transport nanochannel from entering the respective sensing nanochannel.

17. The device of claim 11, wherein the at least one fluid transport nanochannel comprises a single molecule DNA for analysis as the analyte, and wherein at least one of the at least one sensing nanochannel resides at a location away from a mouth of the at least one fluid transport nanochannel that allows the DNA molecule to be fully threaded therein.

* * * * *

UNITED STATES PATENT AND TRADEMARK OFFICE
CERTIFICATE OF CORRECTION

PATENT NO. : 11,053,535 B2
APPLICATION NO. : 14/342032
DATED : July 6, 2021
INVENTOR(S) : Ramsey et al.

Page 1 of 1

It is certified that error appears in the above-identified patent and that said Letters Patent is hereby corrected as shown below:

In the Specification

Column 1, Lines 17-20: Please delete the entire paragraph under the heading, STATEMENT OF FEDERAL SUPPORT, and replace with the following:
This invention was made with government support under Grant No. HG002647 awarded by the National Institutes of Health. The government has certain rights in the invention.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*